United States Patent
Tsutano

(10) Patent No.: US 12,025,603 B2
(45) Date of Patent: Jul. 2, 2024

(54) METHOD FOR ANALYZING METAL IMPURITY CONTENT AND KIT FOR ANALYZING METAL IMPURITY CONTENT

(71) Applicant: ORGANO CORPORATION, Tokyo (JP)

(72) Inventor: Kyohei Tsutano, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 825 days.

(21) Appl. No.: 17/053,254

(22) PCT Filed: May 15, 2019

(86) PCT No.: PCT/JP2019/019347
§ 371 (c)(1),
(2) Date: Nov. 5, 2020

(87) PCT Pub. No.: WO2019/221186
PCT Pub. Date: Nov. 21, 2019

(65) Prior Publication Data
US 2021/0247373 A1    Aug. 12, 2021

(30) Foreign Application Priority Data
May 17, 2018  (JP) .................. 2018-095622

(51) Int. Cl.
*G01N 33/18* (2006.01)
*B01J 39/05* (2017.01)
(Continued)

(52) U.S. Cl.
CPC ......... *G01N 33/1813* (2013.01); *B01J 39/05* (2017.01); *B01J 39/20* (2013.01);
(Continued)

(58) Field of Classification Search
CPC ..... G01N 33/1813; G01N 30/96; B01J 39/05; B01J 39/20; B01J 41/04; B01J 41/14
See application file for complete search history.

(56) References Cited

U.S. PATENT DOCUMENTS

2015/0192556 A1* 7/2015 Sadar ................ G01N 21/47
436/84

FOREIGN PATENT DOCUMENTS

| JP | 56-151351 | 11/1981 |
|---|---|---|
| JP | 5-45351 | 2/1993 |

(Continued)

OTHER PUBLICATIONS

Second Office Action issued in corresponding Chinese Patent Application No. 201980020110.5 dated Aug. 23, 2022, along with English translation thereof.

(Continued)

*Primary Examiner* — Jill A Warden
*Assistant Examiner* — Alex Ramirez
(74) *Attorney, Agent, or Firm* — GREENBLUM & BERNSTEIN, P.L.C.

(57) ABSTRACT

Provided is a method for analyzing the metal impurity content that includes passing water to be analyzed through a monolithic organic porous anion exchanger, thereby allowing the monolithic organic porous anion exchanger to capture metal impurities in the water to be analyzed; passing an eluent through the monolithic organic porous anion exchanger which has been allowed to capture metal impurities in the water to be analyzed, to collect an effluent, thereby obtaining a collected eluent containing metal impurities in the water to be analyzed eluted from the monolithic organic porous anion exchanger; and measuring the content of each metal impurity in the collected eluent.

5 Claims, 3 Drawing Sheets

(51) Int. Cl.
*B01J 39/20* (2006.01)
*B01J 41/04* (2017.01)
*B01J 41/14* (2006.01)
*G01N 30/96* (2006.01)

(52) U.S. Cl.
CPC .............. *B01J 41/04* (2013.01); *B01J 41/14* (2013.01); *G01N 30/96* (2013.01)

(56) References Cited

FOREIGN PATENT DOCUMENTS

| | | | |
|---|---|---|---|
| JP | 7-12787 | | 1/1995 |
| JP | 2001-153854 | | 6/2001 |
| JP | 2010-243476 | | 10/2010 |
| JP | 2010-64344 | A | 11/2010 |
| JP | 2012-506799 | | 3/2012 |
| JP | 2014055974 | A * | 3/2014 |

OTHER PUBLICATIONS

Bunseki Kagaku, "Development of High-Throughput Analysis System Using Highly-Functional Organic Polymer Monoliths", Umemura, Tomonori et al., The Japan Society for Analytical Chemistry, vol. 57, 2008, pp. 517-529, along with partial translation.

Official Communication issued in International Patent Application No. PCT/JP2019/019347, dated Aug. 13, 2019, along with an English translation thereof.

Office Action issued in corresponding Indian Patent Application No. 202017048379 dated Mar. 19, 2021, along with English Translation thereof.

Umemura, "Development of high-throughput Analysis System Using Highly-Functional Organic Polymer Monoliths" Bunseki Kagaku, 2008, vol. 57, No. 7, pp. 517-529, ISSN 0525-1931, https://doi.org/10.2116/bunsekikagaku.57.517.

* cited by examiner

METHOD FOR ANALYZING METAL IMPURITY CONTENT AND KIT FOR ANALYZING METAL IMPURITY CONTENT

TECHNICAL FIELD

The present invention relates to an analytical method for analyzing the content of metal impurities contained at a trace amount in ultrapure water or process water used in the ultrapure water production process, and to an analytical kit used therefor.

BACKGROUND ART

In the semiconductor production process and the pharmaceutical production process, ultrapure water with an extremely low content of ionic impurities is used. Thus, in the production of ultrapure water used in the semiconductor production process and the pharmaceutical production process, it is important to understand the content of ionic impurities that are contained at a trace amount in ultrapure water that is finally produced or in process water of the ultrapure water production process.

In addition, although the type and form of metal impurities in ultrapure water are not known, they may not only be present as ions but also as fine particles in an aggregated or dispersed state.

In the measurement of the concentration of ionic impurities in water, if the concentration thereof is equal to or below the lower detection limit of the measuring instrument, the water to be analyzed is distilled and concentrated in a clean room with a special apparatus and then measurement is carried out (distillation method).

Alternatively, another method is to pass the water to be analyzed through an ion exchanger such as a porous membrane having an ion exchange function or an ion exchange resin, elute the captured ionic impurities with an eluent, and measure the concentration of the ionic impurities in the collected eluent (concentration method). For example, Patent Literature 1 discloses an analytical method based on the concentration method using a porous membrane having an ion exchange function.

CITATION LIST

Patent Literature

[Patent Literature 1] Japanese Patent Laid-Open No. 5-45351

SUMMARY OF INVENTION

Technical Problem

However, in the distillation method, the lower the concentration of ionic impurities, the greater the amount of water to be analyzed to be distilled and the more complicated the operation is. Thus, the possibility of causing contamination is increased, which is problematic. Also, there is a risk of volatilization of some elements.

Meanwhile, the concentration method uses a porous membrane or ion exchange resin for concentration, which results in a high differential pressure and makes it impossible to achieve a high flow rate upon passing the liquid. Thus, there is a problem that the water to be analyzed has to be passed through the porous membrane or ion exchange resin for a long period of time. Alternatively, if the water to be analyzed is allowed to pass through the porous membrane or ion exchange resin at a high flow rate, there is a problem that a short path may occur. Moreover, there is a problem that, due to the high acid concentration of the eluent used to elute the ionic impurity elements captured by the porous membrane or ion exchange resin, the lower limit of quantification is high, and therefore, it is necessary to increase the amount of water passing through the membrane or ion exchange resin, and furthermore, the passing time becomes longer.

In addition, the form of metal impurities in ultrapure water may not only be present as ions but also as fine particles. The surface charge density of fine particles is smaller than that of ions, and their electrostatic interaction with the ion exchange resin is smaller.

Here, monolithic organic porous exchangers have a reticulated flow channel, and not only electrostatically interact with fine particles, but also have an effect of physically adsorbing or capturing them. Also, by using monolithic organic porous anion exchangers, metal impurities in a complexed anionic state can be adsorbed or captured. That is, metal impurities in ultrapure water can be effectively adsorbed or captured.

Accordingly, an object of the present invention is to provide a method for analyzing the metal impurity content in which the passing speed of water to be analyzed is high and the acid concentration in an eluent can be lowered.

Solution to Problem

The problem described above is solved by the present invention shown below.

That is, the present invention (1) provides a method for analyzing a metal impurity content, comprising:
- an impurity capturing step (1) of passing water to be analyzed through a monolithic organic porous anion exchanger, thereby allowing the monolithic organic porous anion exchanger to capture metal impurities in the water to be analyzed;
- an elution step (1) of passing an eluent through the monolithic organic porous anion exchanger which has been allowed to capture metal impurities in the water to be analyzed, to collect an effluent, thereby obtaining a collected eluent containing metal impurities in the water to be analyzed eluted from the monolithic organic porous anion exchanger; and
- a measurement step (1) of measuring a content of each metal impurity in the collected eluent.

In addition, the present invention (2) provides a method for analyzing a metal impurity content, comprising:
- an impurity capturing step (2) of passing water to be analyzed through a monolithic organic porous cation exchanger, thereby allowing the monolithic organic porous cation exchanger to capture metal impurities in the water to be analyzed;
- an elution step (2) of passing an eluent through the monolithic organic porous cation exchanger which has been allowed to capture metal impurities in the water to be analyzed, to collect an effluent, thereby obtaining a collected eluent containing metal impurities in the water to be analyzed eluted from the monolithic organic porous cation exchanger; and
- a measurement step (2) of measuring a content of each metal impurity in the collected eluent.

In addition, the present invention (3) provides a method for analyzing a metal impurity content, comprising:
- an impurity capturing step (3) of passing water to be analyzed firstly through a monolithic organic porous cation exchanger and then through a monolithic organic porous anion exchanger, or firstly through a monolithic organic porous anion exchanger and then through a monolithic organic porous cation exchanger, thereby allowing the monolithic organic porous cation exchanger and the monolithic organic porous anion exchanger to capture metal impurities in the water to be analyzed;

an elution step (3) of passing an eluent firstly through the monolithic organic porous cation exchanger and then through the monolithic organic porous anion exchanger which have been allowed to capture metal impurities in the water to be analyzed, or firstly through the monolithic organic porous anion exchanger and then through the monolithic organic porous cation exchanger which have been allowed to capture metal impurities in the water to be analyzed, to collect an effluent, thereby obtaining a collected eluent containing metal impurities in the water to be analyzed eluted from the monolithic organic porous cation exchanger and the monolithic organic porous anion exchanger; and a measurement step (3) of measuring a content of each metal impurity in the collected eluent.

In addition, the present invention (4) provides a kit for analyzing a metal impurity content, comprising:

a flow cell (1) that comprises at least a monolithic organic porous anion exchanger for passing water to be analyzed through the monolithic organic porous anion exchanger; and an integrating flowmeter for calculating an amount of water to be analyzed that has passed through the flow cell.

In addition, the present invention (5) provides a kit for analyzing a metal impurity content, comprising:

a flow cell (2) that comprises at least a monolithic organic porous cation exchanger for passing water to be analyzed through the monolithic organic porous cation exchanger; and an integrating flowmeter for calculating an amount of water to be analyzed that has passed through the flow cell.

In addition, the present invention (6) provides a kit for analyzing a metal impurity content, comprising:

a flow cell (3) that comprises at least a monolithic organic porous cation exchanger in a foregoing stage and a monolithic organic porous anion exchanger in a subsequent stage for passing water to be analyzed firstly through the monolithic organic porous cation exchanger and then through the monolithic organic porous anion exchanger, or that comprises a monolithic organic porous anion exchanger in a foregoing stage and a monolithic organic porous cation exchanger in a subsequent stage for passing water to be analyzed firstly through the monolithic organic porous anion exchanger and then through the monolithic organic porous cation exchanger; and an integrating flowmeter for calculating an amount of water to be analyzed that has passed through the flow cell.

Advantageous Effects of Invention

According to the present invention, a method for analyzing the metal impurity content can be provided, in which the passing speed of water to be analyzed is high and the acid concentration in an eluent can be lowered.

DESCRIPTION OF EMBODIMENTS

Figure 1:
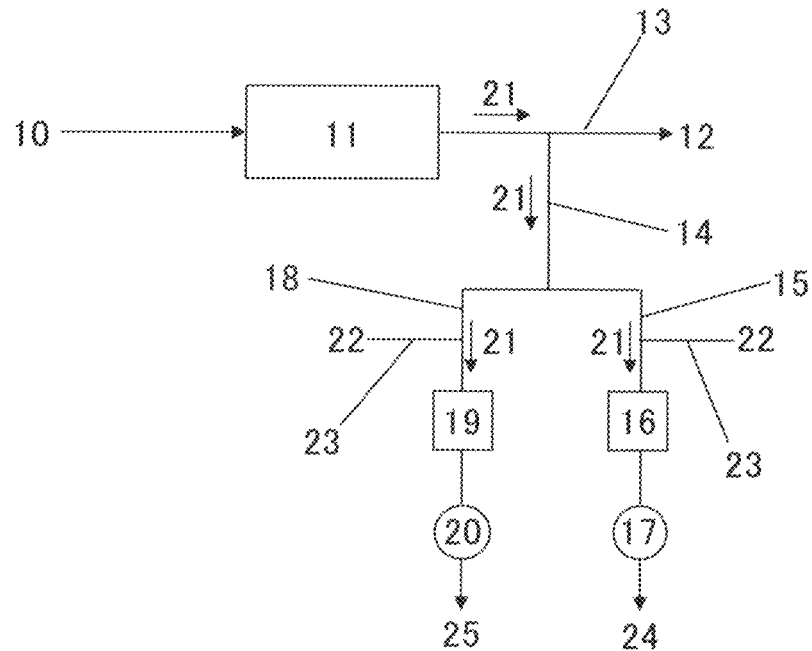
FIG. 1 is a flow diagram of implementing an exemplary embodiment of a method for analyzing the metal impurity content of the present invention.

A method for analyzing the metal impurity content of the first embodiment of the present invention is a method for analyzing the metal impurity content that is characterized by having:

an impurity capturing step (1) of passing water to be analyzed through a monolithic organic porous anion exchanger, thereby allowing the monolithic organic porous anion exchanger to capture metal impurities in the water to be analyzed;

an elution step (1) of passing an eluent through the monolithic organic porous anion exchanger which has been allowed to capture metal impurities in the water to be analyzed, to collect an effluent, thereby obtaining a collected eluent containing metal impurities in the water to be analyzed eluted from the monolithic organic porous anion exchanger; and a measurement step (1) of measuring a content of each metal impurity in the collected eluent.

The method for analyzing the metal impurity content of the first embodiment of the present invention has the impurity capturing step (1), the elution step (1), and the measurement step (1).

The impurity capturing step (1) according to the method for analyzing the metal impurity content of the first embodiment of the present invention is a step of passing water to be analyzed through a monolithic organic porous anion exchanger to allow the water to be analyzed to pass through the inside of the monolithic organic porous anion exchanger while bringing it into contact with the monolithic organic porous anion exchanger, thereby allowing the monolithic organic porous anion exchanger to capture metal impurities in the water to be analyzed.

Examples of the water to be analyzed according to the impurity capturing step (1) include ultrapure water obtained by the ultrapure water production process for producing ultrapure water used at a use point in the semiconductor production process, pharmaceutical production process, or the like, or process water used in the middle of the ultrapure water production process.

Note that, in the present invention, the term "process water used in the middle of the ultrapure water production process" refers to water in general that is generated in the middle of the ultrapure water production process, such as water transferred from the primary pure water production system to the secondary pure water production system in the ultrapure water production process, water transferred from an ultraviolet oxidation apparatus in the secondary pure water production system to a non-regenerative cartridge polisher filled with an ion exchange resin, water transferred from the non-regenerative cartridge polisher filled with an ion exchange resin to a deaeration membrane apparatus, water transferred from the deaeration membrane apparatus to an ultrafiltration membrane apparatus, and water transferred from the ultrafiltration membrane apparatus to a use point (hereinafter the same applies).

The water to be analyzed contains metal impurities of any one or two or more elements selected from B, As, Al, Ti, Cr, Fe, Cu, Zn, Sn, V, Ga, and Pb. In the water to be analyzed, metal impurities are mainly present as ionic impurities of or in a fine particle state of any one or two or more elements selected from B, As, Al, Ti, Cr, Fe, Cu, Zn, Sn, V, Ga, and Pb. The monolithic organic porous anion exchanger exerts excellent performance particularly in capturing B or As. Therefore, the water to be analyzed is preferably water to be analyzed that contains metal impurities of at least any one or two elements selected from B and As.

The water to be analyzed contains, as metal impurities, ionic impurities of any one or two or more elements selected from B, As, Al, Ti, Cr, Fe, Cu, Zn, Sn, V, Ga, and Pb.

In addition, ultrapure water used in the semiconductor production process may contain fine particles. These fine particles are, for example, fine particles originally contained in the raw material water, or fine particles of metal oxides generated from piping materials or joints in the ultrapure water transfer line, and the like. As such, in addition to analyzing the content of ionic impurities in ultrapure water used in the semiconductor production process, it is necessary to analyze the content of such fine particles. The water to be analyzed may contain, as metal impurities, metal fine particles of any one or two or more elements selected from B, As, Al, Ti, Cr, Fe, Cu, Zn, Sn, V, Ga, and Pb. Although the size of the metal fine particles is not particularly limited, it is, for example, 1 to 100 nm.

In addition, the water to be analyzed may contain metal impurities of any one or two or more elements selected from Li, Na, Mg, K, Ca, Mn, Co, Ni, Cd, Ba, and the like. The metal impurities of any one or two or more elements selected from Li, Na, Mg, K, Ca, Mn, Co, Ni, Cd, Ba, and the like are present as ionic impurities, as colloidal or monodispersed fine particles, or in the state of complexes.

Each ionic impurity element is present in the water to be analyzed in a cationic state, in an oxoanionic state, or in a mixed state of cationic and oxoanionic states. In addition, the metal impurity fine particles are present in a colloidal or monodispersed state in the analysis subject.

Although the content of metal impurities in the water to be analyzed is not particularly limited, since the method for analyzing the metal impurity content of the present invention exerts a particularly excellent effect when the metal impurity content is low, the content of each metal impurity in the water to be analyzed is preferably 2000 ng/L or less, more preferably 10 ng/L or less, and particularly preferably 1 ng/L or less.

Details of the monolithic organic porous anion exchanger according to the impurity capturing step (1) will be mentioned later. The ionic form of the monolithic organic porous anion exchanger is not particularly limited and examples thereof include the OH form, the $NO_3$ form, the Cl form, the $CO_3$ form, and the $HCO_3$ form. Among the above, the ionic form of the monolithic organic porous anion exchanger is preferably the OH form because of its high ion exchange adsorption performance.

In the impurity capturing step (1), the amount of water to be analyzed that passes through the monolithic organic porous anion exchanger is selected as appropriate depending on the content of metal impurities in the water to be analyzed, the type and thickness of the monolithic organic porous anion exchanger, the water passing speed, and the like. Note that, when the content of each metal impurity in the water to be analyzed is calculated from the content of each metal impurity in the collected eluent obtained by carrying out the measurement step (1), the total volume of the water to be analyzed that was allowed to pass through the monolithic organic porous anion exchanger is required; therefore, in the impurity capturing step (1), the total amount of the water to be analyzed that was allowed to pass through the monolithic organic porous anion exchanger is measured.

In the impurity capturing step (1), although there is no particular limitation on the passing conditions upon passing the water to be analyzed through the monolithic organic porous anion exchanger, the passing speed SV is preferably 20000 $h^{-1}$ or less, and more preferably 10 to 4000 $h^{-1}$. The lower limit side of SV is particularly preferably 500 $h^{-1}$ or more. In addition, LV is preferably 100 m/h or less, and particularly preferably 1 to 80 m/h. Also, the passing time is selected as appropriate depending on the total passing amount and passing speed of the water to be analyzed.

As described above, in the impurity capturing step (1), metal impurities existing in the state of ionic impurities, colloidal or monodispersed fine particles, complexes, or the like in the water to be analyzed are captured by the monolithic organic porous anion exchanger.

The elution step (1) according to the method for analyzing the metal impurity content of the first embodiment of the present invention is a step of passing an eluent through the monolithic organic porous anion exchanger on which the impurity capturing step (1) has been performed, that is, the monolithic organic porous anion exchanger which has been allowed to capture metal impurities in the water to be analyzed, to allow the eluent to pass through the inside of the monolithic organic porous anion exchanger while bringing it into contact with the monolithic organic porous anion exchanger, thereby obtaining an effluent discharged from the monolithic organic porous anion exchanger, that is, a collected eluent.

The eluent is an aqueous solution containing an acid. The acid contained in the eluent is not particularly limited, and examples thereof include inorganic acids such as nitric acid, sulfuric acid, hydrochloric acid, and phosphoric acid, and organic acids such as methanesulfonic acid. Among the above, the acid contained in the eluent is preferably nitric acid, sulfuric acid, or hydrochloric acid because the ionic impurity elements are readily eluted from the ion exchanger and a reagent with a high purity is required.

Although the acid concentration in the eluent is not particularly limited, the method for analyzing the metal impurity content of the present invention can lower the acid concentration in the eluent, thus lowering the lower limit of quantification. Therefore, the acid concentration in the eluent is preferably 0.1 to 2.0 N, and more preferably 0.5 to 2.0 N, in that the lower limit of quantification becomes lower. When the acid concentration is less than 0.1 N, it is not preferable because the amount of liquid to be collected will be increased. On the other hand, when the acid concentration is greater than 2.0 N, it is not preferable because the lower limit of quantification of the analytical apparatus will become higher. In addition, as the eluent, an eluent with a content of each metal impurity of 100 ppt or less is preferable, nitric acid or hydrochloric acid with a content of each metal impurity of 100 ppt or less is more preferable, and nitric acid or hydrochloric acid with a content of each metal impurity of 10 ppt or less is particularly preferable.

In the elution step (1), the amount of eluent that passes through the monolithic organic porous anion exchanger is selected as appropriate depending on the type and thickness of the monolithic organic porous anion exchanger, the water passing speed, and the like. In the method for analyzing the metal impurity content of the present invention, since the metal impurity elements are readily eluted from the monolithic organic porous anion exchanger, the method for analyzing the metal impurity content of the present invention can reduce the passing amount of the eluent. And the reduction in the passing amount of the eluent leads to a reduction in the measurement time.

In the elution step (1), although there is no particular limitation on the passing conditions upon passing the eluent through the monolithic organic porous anion exchanger, the passing speed SV is preferably 20000 $h^{-1}$ or less, more preferably 10 to 4000 $h^{-1}$, and particularly preferably 300 to 1000 $h^{-1}$. In addition, LV is preferably 100 m/h or less, and particularly preferably 1 to 80 m/h. Also, the passing time is selected as appropriate depending on the total passing amount and passing speed of the eluent.

In the elution step (1), the metal impurities in the water to be analyzed that have been captured by the monolithic organic porous anion exchanger are eluted by the eluent and transferred into the eluent. And, by carrying out the elution step (1), a collected eluent containing the metal impurities in the water to be analyzed is obtained.

The measurement step (1) according to the method for analyzing the metal impurity content of the first embodiment of the present invention is a step of measuring the content of each metal impurity in the collected eluent obtained by carrying out the elution step (1).

There is no particular limitation on the method for measuring the content of each metal impurity in the collected eluent, and examples thereof include a method using a plasma mass spectrometer (ICP-MS), a plasma emission spectrophotometer (ICP), an atomic absorption photometer, and an ion chromatographic analyzer. The measurement conditions are selected as appropriate.

In the method for analyzing the metal impurity content of the first embodiment of the present invention, the content of each metal impurity in the water to be analyzed is determined from the content of each metal impurity in the collected eluent obtained by carrying out the measurement step (1), the collection amount of the collected eluent, and the total passing amount of the water to be analyzed that has passed through the monolithic organic porous anion exchanger in the impurity capturing step (1).

And, in the method for analyzing the metal impurity content of the first embodiment of the present invention, the monolithic organic porous anion exchanger is allowed to capture metal impurities, that is, at least ionic impurity elements and metal impurity fine particles in the water to be analyzed in the impurity capturing step (1), the eluent is passed through the monolithic organic porous anion exchanger to collect the effluent, thereby collecting the collected eluent containing metal impurities, that is, at least ionic impurity elements and metal impurity fine particles in the water to be analyzed, which have been eluted from the monolithic organic porous anion exchanger, in the elution step (1), and the content of each metal impurity in the collected eluent is measured in the measurement step (1). Also, since the method for analyzing the metal impurity content of the first embodiment of the present invention exerts an excellent effect on the analysis of ionic impurity elements and metal impurity fine particles in particular, it is preferable that the water to be analyzed should contain at least ionic impurity elements and metal impurity fine particles as metal impurities.

A method for analyzing the metal impurity content of the second embodiment of the present invention is a method for analyzing the metal impurity content that is characterized by having:
  an impurity capturing step (2) of passing water to be analyzed through a monolithic organic porous cation exchanger, thereby allowing the monolithic organic porous cation exchanger to capture metal impurities in the water to be analyzed;
  an elution step (2) of passing an eluent through the monolithic organic porous cation exchanger which has been allowed to capture metal impurities in the water to be analyzed, to collect an effluent, thereby obtaining a collected eluent containing metal impurities in the water to be analyzed eluted from the monolithic organic porous cation exchanger; and
  a measurement step (2) of measuring a content of each metal impurity in the collected eluent.

The method for analyzing the metal impurity content of the second embodiment of the present invention has the impurity capturing step (2), the elution step (2), and the measurement step (2).

The impurity capturing step (2) according to the method for analyzing the metal impurity content of the second embodiment of the present invention is a step of passing water to be analyzed through a monolithic organic porous cation exchanger to allow the water to be analyzed to pass through the inside of the monolithic organic porous cation exchanger while bringing it into contact with the monolithic organic porous cation exchanger, thereby allowing the monolithic organic porous cation exchanger to capture metal impurities in the water to be analyzed.

Examples of the water to be analyzed according to the impurity capturing step (2) include ultrapure water obtained by the ultrapure water production process for producing ultrapure water used at a use point in the semiconductor production process, pharmaceutical production process, or the like, or process water used in the middle of the ultrapure water production process.

The water to be analyzed contains metal impurities of any one or two or more elements selected from Li, Na, Mg, K, Ca, Mn, Co, Ni, Cd, Ba, and the like. In the water to be analyzed, metal impurities are mainly present as ionic impurities of or in a fine particle state of any one or two or more elements selected from Li, Na, Mg, K, Ca, Mn, Co, Ni, Cd, Ba, and the like.

The water to be analyzed contains, as metal impurities, ionic impurities of any one or two or more elements selected from Li, Na, Mg, K, Ca, Mn, Co, Ni, Cd, Ba, and the like.

Also, ultrapure water used in the semiconductor production process may contain fine particles, and therefore, in addition to analyzing the content of ionic impurities in the ultrapure water used in the semiconductor production process, it is necessary to analyze the content of such fine particles. The water to be analyzed may contain, as metal impurities, metal fine particles of any one or two or more elements selected from Li, Na, Mg, K, Ca, Mn, Co, Ni, Cd, Ba, and the like. Although the size of the metal fine particles is not particularly limited, it is, for example, 1 to 100 nm.

In addition, the water to be analyzed may contain metal impurities of any one or two or more elements selected from B, As, Al, Ti, Cr, Fe, Cu, Zn, Sn, V, Ga, and Pb. The metal impurities formed of any one or two or more elements out of any one or two or more elements selected from B, As, Al, Ti, Cr, Fe, Cu, Zn, Sn, V, Ga, and Pb are present as ionic impurities, as colloidal or monodispersed fine particles, or in the state of complexes.

Each ionic impurity element is present in the water to be analyzed in a cationic state, in an oxoanionic state, or in a mixed state of cationic and oxoanionic states.

Although the content of metal impurities in the water to be analyzed is not particularly limited, since the method for analyzing the metal impurity content of the present invention exerts a particularly excellent effect when the metal impurity content is low, the content of metal impurities in the water to be analyzed is preferably 2000 ng/L or less, more preferably 10 ng/L or less, and particularly preferably 1 ng/L or less.

Details of the monolithic organic porous cation exchanger according to the impurity capturing step (2) will be mentioned later. The ionic form of the monolithic organic porous cation exchanger is not particularly limited and examples thereof include the H form and the Na form. Among the above, the ionic form of the monolithic organic porous cation exchanger is preferably the H form because of its high ion exchange adsorption performance.

In the impurity capturing step (2), the amount of water to be analyzed that passes through the monolithic organic porous cation exchanger is selected as appropriate depending on the content of metal impurities in the water to be analyzed, the type and thickness of the monolithic organic porous cation exchanger, the water passing speed, and the like. Note that, when the content of each metal impurity in the water to be analyzed is calculated from the content of each metal impurity in the collected eluent obtained by carrying out the measurement step (2), the total volume of the water to be analyzed that was allowed to pass through the monolithic organic porous cation exchanger is required; therefore, in the impurity capturing step (2), the total amount of the water to be analyzed that was allowed to pass through the monolithic organic porous cation exchanger is measured.

In the impurity capturing step (2), although there is no particular limitation on the passing conditions upon passing the water to be analyzed through the monolithic organic porous cation exchanger, the passing speed SV is preferably 20000 $h^{-1}$ or less, and more preferably 10 to 4000 $h^{-1}$. The lower limit side of SV is particularly preferably 500 $h^{-1}$ or more. In addition, LV is preferably 100 m/h or less, and particularly preferably 1 to 80 m/h. Also, the passing time is selected as appropriate depending on the total passing amount and passing speed of the water to be analyzed.

As described above, in the impurity capturing step (2), metal impurities existing in the state of ionic impurities, colloidal or monodispersed fine particles, complexes, or the like in the water to be analyzed are captured by the monolithic organic porous cation exchanger.

The elution step (2) according to the method for analyzing the metal impurity content of the second embodiment of the present invention is a step of passing an eluent through the monolithic organic porous cation exchanger on which the impurity capturing step (2) has been performed, that is, the monolithic organic porous cation exchanger which has been allowed to capture metal impurity elements in the water to be analyzed, to allow the eluent to pass through the inside of the monolithic organic porous cation exchanger while bringing it into contact with the monolithic organic porous anion exchanger, thereby obtaining an effluent discharged from the monolithic organic porous cation exchanger, that is, a collected eluent.

The eluent is an aqueous solution containing an acid. The acid contained in the eluent is not particularly limited, and examples thereof include inorganic acids such as nitric acid, sulfuric acid, hydrochloric acid, and phosphoric acid, and methanesulfonic acid. Among the above, the acid contained in the eluent is preferably nitric acid, sulfuric acid, or hydrochloric acid because the ionic impurity elements are readily eluted from the ion exchanger and a reagent with a high purity is required.

Although the acid concentration in the eluent is not particularly limited, the method for analyzing the metal impurity content of the present invention can lower the acid concentration in the eluent, thus lowering the lower limit of quantification. Therefore, the acid concentration in the eluent is preferably 0.1 to 2.0 N, and more preferably 0.5 to 2.0 N, in that the lower limit of quantification becomes lower. When the acid concentration is less than 0.1 N, it is not preferable because the amount of liquid to be collected will be increased. On the other hand, when the acid concentration is greater than 2.0 N, it is not preferable because the lower limit of quantification of the analytical apparatus will become higher. In addition, as the eluent, an eluent with a content of each metal impurity of 100 ppt or less is preferable, nitric acid or hydrochloric acid with a content of each metal impurity of 100 ppt or less is more preferable, and nitric acid or hydrochloric acid with a content of each metal impurity of 10 ppt or less is particularly preferable.

In the elution step (2), the amount of eluent that passes through the monolithic organic porous cation exchanger is selected as appropriate depending on the type and thickness of the monolithic organic porous cation exchanger, and the water passing speed. In the method for analyzing the metal impurity content of the present invention, since the metal impurity elements are readily eluted from the monolithic organic porous cation exchanger, the method for analyzing the metal impurity content of the present invention can reduce the passing amount of the eluent. And the reduction in the passing amount of the eluent leads to a reduction in the measurement time.

In the elution step (2), although there is no particular limitation on the passing conditions upon passing the eluent through the monolithic organic porous cation exchanger, the passing speed SV is preferably 20000 $h^{-1}$ or less, more preferably 10 to 4000 $h^{-1}$, and particularly preferably 300 to 1000 $h^{-1}$. In addition, LV is preferably 100 m/h or less, and particularly preferably 1 to 80 m/h. Also, the passing time is selected as appropriate depending on the total passing amount and passing speed of the eluent.

In the elution step (2), the metal impurity elements in the water to be analyzed that have been captured by the monolithic organic porous cation exchanger are eluted by the eluent and transferred into the eluent. And, by carrying out the elution step (2), a collected eluent containing the metal impurity elements in the water to be analyzed is obtained.

The measurement step (2) according to the method for analyzing the metal impurity content of the second embodiment of the present invention is a step of measuring the content of each metal impurity in the collected eluent obtained by carrying out the elution step (2).

There is no particular limitation on the method for measuring the content of each metal impurity in the collected eluent, and examples thereof include a method using a plasma mass spectrometer (ICP-MS), a plasma emission spectrophotometer (ICP), an atomic absorption photometer, and an ion chromatographic analyzer. The measurement conditions are selected as appropriate.

In the method for analyzing the metal impurity content of the second embodiment of the present invention, the content of each metal impurity in the water to be analyzed is determined from the content of each metal impurity in the collected eluent obtained by carrying out the measurement step (2), the collection amount of the collected eluent, and the total passing amount of the water to be analyzed that has passed through the monolithic organic porous cation exchanger in the impurity capturing step (2).

And, in the method for analyzing the metal impurity content of the second embodiment of the present invention, the monolithic organic porous cation exchanger is allowed to capture metal impurities, that is, at least ionic impurity elements and metal impurity fine particles in the water to be analyzed in the impurity capturing step (2), the eluent is passed through the monolithic organic porous cation exchanger to collect the effluent, thereby collecting the collected eluent containing metal impurities, that is, at least ionic impurity elements and metal impurity fine particles in the water to be analyzed, which have been eluted from the monolithic organic porous cation exchanger, in the elution step (2), and the content of each metal impurity in the collected eluent is measured in the measurement step (2). Also, since the method for analyzing the metal impurity content of the second embodiment of the present invention exerts an excellent effect on the analysis of ionic impurity elements and metal impurity fine particles in particular, it is preferable that the water to be analyzed should contain at least ionic impurity elements and metal impurity fine particles as metal impurities.

A method for analyzing the metal impurity content of the third embodiment of the present invention is a method for analyzing the metal impurity content that is characterized by having:

an impurity capturing step (3) of passing water to be analyzed firstly through a monolithic organic porous cation exchanger and then through a monolithic organic porous anion exchanger, or firstly through a monolithic organic porous anion exchanger and then through a monolithic organic porous cation exchanger, thereby allowing the monolithic organic porous cation exchanger and the monolithic organic porous anion exchanger to capture metal impurities in the water to be analyzed;

an elution step (3) of passing an eluent firstly through the monolithic organic porous cation exchanger and then through the monolithic organic porous anion exchanger which have been allowed to capture metal impurities in the water to be analyzed, or firstly through the monolithic organic porous anion exchanger and then through the monolithic organic porous cation exchanger which have been allowed to capture metal impurities in the water to be analyzed, to collect an effluent, thereby obtaining a collected eluent containing metal impurities in the water to be analyzed eluted from the monolithic organic porous cation exchanger and the monolithic organic porous anion exchanger; and a measurement step (3) of measuring a content of each metal impurity in the collected eluent.

The method for analyzing the metal impurity content of the third embodiment of the present invention has the impurity capturing step (3), the elution step (3), and the measurement step (3).

The impurity capturing step (3) according to the method for analyzing the metal impurity content of the third embodiment of the present invention is a step of passing water to be analyzed through a monolithic organic porous cation exchanger and a monolithic organic porous anion exchanger to allow the water to be analyzed to pass through the inside of the monolithic organic porous cation exchanger and the monolithic organic porous anion exchanger while bringing it into contact with the monolithic organic porous cation exchanger and the monolithic organic porous anion exchanger, thereby allowing the monolithic organic porous cation exchanger and the monolithic organic porous anion exchanger to capture metal impurities in the water to be analyzed.

Examples of the water to be analyzed according to the impurity capturing step (3) include ultrapure water obtained by the ultrapure water production process for producing ultrapure water used at a use point in the semiconductor production process, pharmaceutical production process, or the like, or process water used in the middle of the ultrapure water production process.

The water to be analyzed at least contains metal impurities of any one or two or more elements selected from Li, Na, Mg, K, Ca, Mn, Co, Ni, Cd, and Ba, and metal impurities of any one or two or more elements selected from B, As, Al, Ti, Cr, Fe, Cu, Zn, Sn, V, Ga, and Pb. The monolithic organic porous anion exchanger exerts excellent performance particularly in capturing B or As. Therefore, the water to be analyzed is preferably water to be analyzed that at least contains metal impurities of any one or two or more elements selected from Li, Na, Mg, K, Ca, Mn, Co, Ni, Cd, Ba, and the like, and metal impurities of any one or two or more elements selected from B and As. In the water to be analyzed, metal impurities are mainly present as ionic impurities of or in a fine particle state of the elements described above.

The water to be analyzed contains, as metal impurities, ionic impurities of any one or two or more elements selected from Li, Na, Mg, K, Ca, Mn, Co, Ni, Cd, and Ba, and ionic impurities of any one or two or more elements selected from B, As, Al, Ti, Cr, Fe, Cu, Zn, Sn, V, Ga, and Pb.

Also, ultrapure water used in the semiconductor production process may contain fine particles, and therefore, in addition to analyzing the content of ionic impurities in the ultrapure water used in the semiconductor production process, it is necessary to analyze the content of such fine particles. The water to be analyzed may contain, as metal impurities, metal impurity fine particles of any one or two or more elements selected from Li, Na, Mg, K, Ca, Mn, Co, Ni, Cd, and Ba, and metal impurity fine particles of any one or two or more elements selected from B, As, Al, Ti, Cr, Fe, Cu, Zn, Sn, V, Ga, and Pb. Although the size of the metal impurity fine particles is not particularly limited, it is, for example, 1 to 100 nm.

Each ionic impurity element is present in the water to be analyzed in a cationic state, in an oxoanionic state, or in a mixed state of cationic and oxoanionic states.

Although the content of metal impurities in the water to be analyzed is not particularly limited, since the method for analyzing the metal impurity content of the present invention exerts a particularly excellent effect when the metal impurity content is low, the content of metal impurities in the water to be analyzed is preferably 2000 ng/L or less, more preferably 10 ng/L or less, and particularly preferably 1 ng/L or less.

Details of the monolithic organic porous cation exchanger and the monolithic organic porous anion exchanger according to the impurity capturing step (3) will be mentioned later. The ionic form of the monolithic organic porous cation exchanger is not particularly limited and examples thereof include the H form, the Cl form, the $CO_3$ form, and the $HCO_3$ form. Among the above, the ionic form of the monolithic organic porous cation exchanger is preferably the H form because of its high ion exchange adsorption performance. The ionic form of the monolithic organic porous anion exchanger is not particularly limited and examples thereof include the OH form, the $NO_3$ form, the Cl form, the $CO_3$ form, and the $HCO_3$ form. Among the above, the ionic form of the monolithic organic porous anion exchanger is preferably the OH form because of its high ion exchange adsorption performance.

In the impurity capturing step (3), (i) water to be analyzed is firstly passed through a monolithic organic porous cation exchanger to pass through the inside of the monolithic organic porous cation exchanger, and an effluent from the monolithic organic porous cation exchanger is then passed through a monolithic organic porous anion exchanger to pass through the inside of the monolithic organic porous anion exchanger, or (ii) water to be analyzed is firstly passed through a monolithic organic porous anion exchanger to pass through the inside of the monolithic organic porous anion exchanger, and an effluent from the monolithic organic porous anion exchanger is then passed through a monolithic organic porous cation exchanger to pass through the inside of the monolithic organic porous cation exchanger.

In the impurity capturing step (3), the amount of water to be analyzed that passes through the monolithic organic porous cation exchanger and the monolithic organic porous anion exchanger is selected as appropriate depending on the content of metal impurities in the water to be analyzed, the type and thickness of the monolithic organic porous cation exchanger and the monolithic organic porous anion exchanger, the water passing speed, and the like. Note that, when the content of each metal impurity in the water to be analyzed is calculated from the content of each metal impurity in the collected eluent obtained by carrying out the measurement step (3), the total volume of the water to be analyzed that was allowed to pass through the monolithic organic porous cation exchanger and the monolithic organic porous anion exchanger is required; therefore, in the impurity capturing step (3), the total amount of the water to be analyzed that was allowed to pass through the monolithic organic porous cation exchanger and the monolithic organic porous anion exchanger is measured.

In the impurity capturing step (3), although there is no particular limitation on the passing conditions upon passing the water to be analyzed through the monolithic organic porous cation exchanger and the monolithic organic porous anion exchanger, the passing speed SV is preferably 20000 $h^{-1}$ or less, and more preferably 10 to 4000 $h^{-1}$. The lower limit side of SV is particularly preferably 500 $h^{-1}$ or more. In addition, LV is preferably 100 m/h or less, and particularly preferably 1 to 80 m/h. Also, the passing time is selected as appropriate depending on the total passing amount and passing speed of the water to be analyzed.

As described above, in the impurity capturing step (3), metal impurities existing in the state of ionic impurities, colloidal or monodispersed fine particles, complexes, or the like in the water to be analyzed are captured by the monolithic organic porous cation exchanger and the monolithic organic porous anion exchanger.

The elution step (3) according to the method for analyzing the metal impurity content of the third embodiment of the present invention is a step of passing an eluent through the monolithic organic porous cation exchanger and the monolithic organic porous anion exchanger on which the impurity capturing step (3) has been performed, that is, the monolithic organic porous cation exchanger and the monolithic organic porous anion exchanger which have been allowed to capture metal impurities in the water to be analyzed, to allow the eluent to pass through the inside of the monolithic organic porous cation exchanger and the inside of the monolithic organic porous anion exchanger while bringing it into contact with the monolithic organic porous cation exchanger and the monolithic organic porous anion exchanger, thereby obtaining an effluent discharged from the subsequent monolithic organic porous ion exchanger, that is, a collected eluent.

In the elution step (3), (i) the eluent is firstly passed through the monolithic organic porous cation exchanger which has been allowed to capture metal impurities in the water to be analyzed, to pass through the inside of the monolithic organic porous cation exchanger, and an effluent from the monolithic organic porous cation exchanger is then passed through the monolithic organic porous anion exchanger which have been allowed to capture metal impurities in the water to be analyzed, to pass through the inside of the monolithic organic porous anion exchanger, or (ii) the eluent is firstly passed through the monolithic organic porous anion exchanger which has been allowed to capture metal impurities in the water to be analyzed, to pass through the inside of the monolithic organic porous anion exchanger, and an effluent from the monolithic organic porous anion exchanger is then passed through a monolithic organic porous cation exchanger which have been allowed to capture metal impurities in the water to be analyzed, to pass through the inside of the monolithic organic porous cation exchanger.

The eluent is an aqueous solution containing an acid. The acid contained in the eluent is not particularly limited, and examples thereof include inorganic acids such as nitric acid, sulfuric acid, hydrochloric acid, and phosphoric acid, and organic acids such as methanesulfonic acid. Among the above, the acid contained in the eluent is preferably nitric acid, sulfuric acid, or hydrochloric acid because the ionic impurity elements are readily eluted from the ion exchanger.

Although the acid concentration in the eluent is not particularly limited, the method for analyzing the metal impurity content of the present invention can lower the acid concentration in the eluent, thus lowering the lower limit of quantification. Therefore, the acid concentration in the eluent is preferably 0.1 to 2.0 N, and more preferably 0.5 to 2.0 N, in that the lower limit of quantification becomes lower. When the acid concentration is less than 0.1 N, it is not preferable because the amount of liquid to be collected will be increased. On the other hand, when the acid concentration is greater than 2.0 N, it is not preferable because the lower limit of quantification of the analytical apparatus will become higher. In addition, as the eluent, an eluent with a content of each metal impurity of 100 ppt or less is preferable, nitric acid or hydrochloric acid with a content of each metal impurity of 100 ppt or less is more preferable, and nitric acid or hydrochloric acid with a content of each metal impurity of 10 ppt or less is particularly preferable.

In the elution step (3), the amount of eluent that passes through the monolithic organic porous cation exchanger and the monolithic organic porous anion exchanger is selected as appropriate depending on the type and thickness of the monolithic organic porous cation exchanger and the monolithic organic porous anion exchanger, the water passing speed, and the like. In the method for analyzing the metal impurity content of the present invention, since the metal impurities are readily eluted from the monolithic organic porous cation exchanger and the monolithic organic porous anion exchanger, the method for analyzing the metal impurity content of the present invention can reduce the passing amount of the eluent. And the reduction in the passing amount of the eluent leads to a reduction in the measurement time.

In the elution step (3), although there is no particular limitation on the passing conditions upon passing the eluent through the monolithic organic porous cation exchanger and the monolithic organic porous anion exchanger, the passing speed SV is preferably 20000 $h^{-1}$ or less, more preferably 10 to 4000 $h^{-1}$, and particularly preferably 300 to 1000 $h^{-1}$. In addition, LV is preferably 100 m/h or less, and particularly preferably 1 to 80 m/h. Also, the passing time is selected as appropriate depending on the total passing amount and passing speed of the eluent.

In the elution step (3), the metal impurity elements in the water to be analyzed that have been captured by the monolithic organic porous cation exchanger or the monolithic organic porous anion exchanger are eluted by the eluent and transferred into the eluent. And, by carrying out the elution step (3), a collected eluent containing the metal impurity elements in the water to be analyzed is obtained.

The measurement step (3) according to the method for analyzing the metal impurity content of the third embodiment of the present invention is a step of measuring the content of each metal impurity in the collected eluent obtained by carrying out the elution step (3).

There is no particular limitation on the method for measuring the content of each metal impurity in the collected eluent, and examples thereof include a method using a plasma mass spectrometer (ICP-MS), a plasma emission spectrophotometer (ICP), an atomic absorption photometer, and an ion chromatographic analyzer. The measurement conditions are selected as appropriate.

In the method for analyzing the metal impurity content of the third embodiment of the present invention, the content of each metal impurity in the water to be analyzed is determined from the content of each metal impurity in the collected eluent obtained by carrying out the measurement step (3), the collection amount of the collected eluent, and the total passing amount of the water to be analyzed that has passed through the monolithic organic porous cation exchanger and the monolithic organic porous anion exchanger in the impurity capturing step (3).

And, in the method for analyzing the metal impurity content of the third embodiment of the present invention, the monolithic organic porous cation exchanger and the monolithic organic porous anion exchanger is allowed to capture metal impurities, that is, at least ionic impurity elements and metal impurity fine particles in the water to be analyzed in the impurity capturing step (3), the eluent is passed through the monolithic organic porous cation exchanger and the monolithic organic porous anion exchanger to collect the effluent, thereby collecting the collected eluent containing metal impurities, that is, at least ionic impurity elements and metal impurity fine particles in the water to be analyzed, which have been eluted from the monolithic organic porous cation exchanger and the monolithic organic porous anion exchanger, in the elution step (3), and the content of each metal impurity in the collected eluent is measured in the measurement step (3).

In a variation of the method for analyzing the metal impurity content of the third embodiment of the present invention, the monolithic organic porous cation exchanger or the monolithic organic porous anion exchanger, specifically, one of the monolithic organic porous cation exchanger or the monolithic organic porous anion exchanger through which water to be analyzed is firstly passed, is allowed to capture metal impurities in the water to be analyzed, that is, not only ionic impurity elements but also metal impurity fine particles in the water to be analyzed in the impurity capturing step (3), the eluent is passed through the monolithic organic porous cation exchanger and the monolithic organic porous anion exchanger to collect the effluent, thereby collecting the collected eluent containing metal impurities in the water to be analyzed, that is, at least ionic impurity elements and metal impurity fine particles in the water to be analyzed, which have been eluted from the monolithic organic porous cation exchanger and the monolithic organic porous anion exchanger, in the elution step (3), and the content of each metal impurity in the collected eluent is measured in the measurement step (3). Also, since the method for analyzing the metal impurity content of the third embodiment of the present invention exerts an excellent effect on the analysis of ionic impurity elements and metal impurity fine particles in particular, it is preferable that the water to be analyzed should contain at least ionic impurity elements and metal impurity fine particles as metal impurities.

Hereinafter, an exemplary embodiment of the method for analyzing the metal impurity content of the present invention will be described. For example, as illustrated in FIG. 1, in the ultrapure water production process where raw material water 10 is supplied to an ultrapure water production apparatus 11 and ultrapure water 21 obtained in the ultrapure water production apparatus 11 is supplied to a use point 12, an analysis system is constructed as follows. A pipe for withdrawing water to be analyzed 14 is linked to the middle of a pipe for transferring ultrapure water 13 for transferring the ultrapure water 21 to the use point 12, and the other end side of the pipe for withdrawing water to be analyzed 14 is branched into a first branched pipe 15 and a second branched pipe 18. To the first branched pipe 15, a flow cell 16 comprising a monolithic organic porous anion exchanger and an integrating flowmeter 17 are installed, and to the second branched pipe 18, a flow cell 19 comprising a monolithic organic porous cation exchanger and an integrating flowmeter 20 are installed. Also, an introduction pipe 23 for an eluent 22 is connected to each of the first branched pipe 15 and the second branched pipe 18. And, when the ultrapure water production process is being carried out, the ultrapure water 21, which is the water to be analyzed, is passed through the pipe for transferring ultrapure water 13, the pipe for withdrawing water to be analyzed 14, the first branched pipe 15, and finally the flow cell 16 to carry out an impurity capturing step (1), and the ultrapure water 21, which is the water to be analyzed, is also passed through the pipe for transferring ultrapure water 13, the pipe for withdrawing water to be analyzed 14, the second branched pipe 18, and finally the flow cell 19 to carry out an impurity capturing step (2). Upon this, the total passing amounts of ultrapure water to the flow cell 16 and the flow cell 19 are measured by the integrating flowmeter 17 and the integrating flowmeter 20, respectively. Note that, to prevent the ultrapure water 21 from flowing into the introduction pipe 23 for the eluent 22, the flow is controlled by a valve not illustrated in the figure. Next, after passing a predetermined amount of ultrapure water, the eluent is supplied at a predetermined amount from the introduction pipe 23 for the eluent linked to the first branched pipe 15 or the second branched pipe 18, and the eluent 22 is passed through the flow cell 16 and the flow cell 19 to collect the collected eluent 24 and 25, respectively, to carry out an elution step (1)

and an elution step (2). Subsequently, the content of each metal impurity in each of the collected eluents 24 and 25 is measured to carry out a measurement step (1) and a measurement step (2), respectively. Then, based on the above results, the content of each metal impurity in the ultrapure water 21 is determined. In this way, the method for analyzing the metal impurity content of the first embodiment of the present invention and the method for analyzing the metal impurity content of the second embodiment of the present invention are carried out in parallel.

Figure 2:
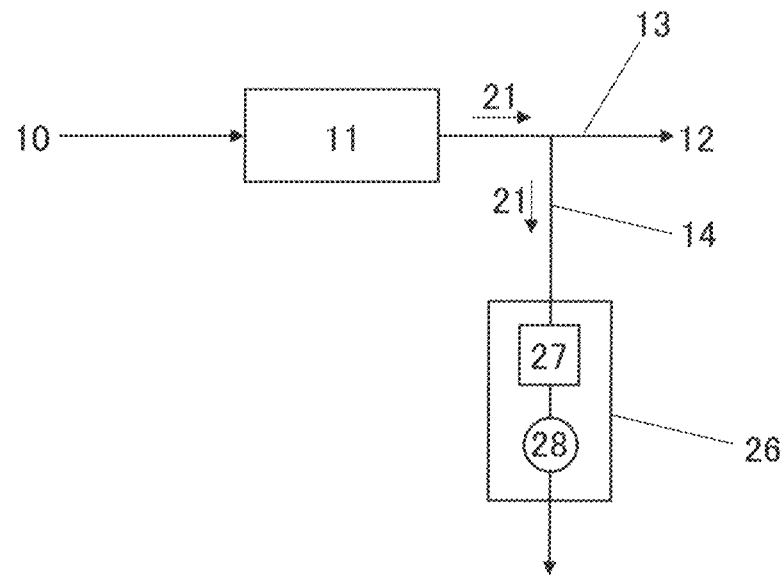
FIG. 2 is a flow diagram of implementing an exemplary embodiment of a method for analyzing the metal impurity content of the present invention.

Another exemplary embodiment of the method for analyzing the metal impurity content of the present invention will be described. For example, as illustrated in FIG. 2, in the ultrapure water production process where raw material water 10 is supplied to an ultrapure water production apparatus 11 and ultrapure water 21 obtained in the ultrapure water production apparatus 11 is supplied to a use point 12, a pipe for withdrawing water to be analyzed 14 is linked to the middle of a pipe for transferring ultrapure water 13 for transferring the ultrapure water 21 to the use point 12, and to the pipe for withdrawing water to be analyzed 14, an analytical kit 26 is attached that has a flow cell 27 comprising a monolithic organic porous cation exchanger in the foregoing stage and a monolithic organic porous anion exchanger in a stage subsequent thereto, and an integrating flowmeter 28. And, when the ultrapure water production process is being carried out, the ultrapure water 21, which is the water to be analyzed, is passed through the pipe for transferring ultrapure water 13 and the pipe for withdrawing water to be analyzed 14, and supplied to the flow cell 27, thereby passing the ultrapure water 21 firstly through the monolithic organic porous cation exchanger in the foregoing stage and then passing an effluent from the monolithic organic porous cation exchanger through the monolithic organic porous anion exchanger in the subsequent stage to carry out an impurity capturing step (3). Upon this, the total passing amount of ultrapure water to the flow cell 27 is measured by the integrating flowmeter 28. Next, after passing a predetermined amount of ultrapure water, the analytical kit 26 is detached from the pipe for withdrawing water to be analyzed 14. Upon this, while removing the analytical kit 26 in a manner that does not cause external contamination to the inside thereof, the inside is sealed. Subsequently, the analytical kit 26 is attached to an elution apparatus that is provided at a different location from the location where the ultrapure water production process is being carried out. An eluent is firstly passed through the monolithic organic porous cation exchanger in the analytical kit 26 via an eluent supply pipe of the elution apparatus, and an effluent therefrom is passed through the monolithic organic porous anion exchanger to collect a collected eluent from the analytical kit 26, thereby carrying out an elution step (3). Then, the content of metal impurities in the collected eluent is measured to carry out a measurement step (3). And, based on the above results, the content of each metal impurity in the ultrapure water 21 is determined. In this way, the method for analyzing the metal impurity content of the third embodiment of the present invention is carried out.

In the method for analyzing the metal impurity content of the present invention, the impurity capturing step ((1), (2), or (3)), the elution step ((1), (2), or (3)), and the analysis step ((1), (2), or (3)) may all be carried out at a location where the production of the water to be analyzed is carried out, or the elution step ((1), (2), or (3)) and the analysis step ((1), (2), or (3)) may be carried out at a different location from that for the impurity capturing step ((1), (2), or (3)), or the impurity capturing step ((1), (2), or (3)) and the elution step ((1), (2), or (3)) may be carried out at the same location and the analysis step ((1), (2), or (3)) may be carried out at different location from the location where the above two steps are carried out, or the impurity capturing step ((1), (2), or (3)), the elution step ((1), (2), or (3)), and the analysis step ((1), (2), or (3)) may each be carried out at a different location.

The monolithic organic porous anion exchanger according to the present invention is a porous material formed by introducing anion exchange groups into a monolithic organic porous material. The monolithic organic porous material according to the monolithic organic porous anion exchanger is a porous material that has a framework formed of an organic polymer, and has a number of communication holes in the framework that serve as flow channels for the reaction liquid. And, the monolithic organic porous anion exchanger is a porous material formed by introducing anion exchange groups into the framework of this monolithic organic porous material such that the anion exchange groups are uniformly distributed therein. Also, the monolithic organic porous cation exchanger according to the present invention is a porous material formed by introducing cation exchange groups into a monolithic organic porous material. The monolithic organic porous material according to the monolithic organic porous cation exchanger is a porous material that has a framework formed of an organic polymer, and has a number of communication holes in the framework that serve as flow channels for the reaction liquid. And, the monolithic organic porous cation exchanger is a porous material formed by introducing cation exchange groups into the framework of this monolithic organic porous material such that the cation exchange groups are uniformly distributed therein.

Note that, in the present specification, the "monolithic organic porous material" may also be simply referred to as a "monolith", the "monolithic organic porous anion exchanger" may also be simply referred to as a "monolithic anion exchanger", and the "monolithic organic porous cation exchanger" may also be simply referred to as a "monolithic cation exchanger". Furthermore, a "monolithic organic porous intermediate (2)", which is an intermediate in the production of a second monolith (a precursor of the second monolith), may also be simply referred to as a "monolithic intermediate (2)".

The monolithic anion exchanger according to the present invention is obtained by introducing anion exchange groups into a monolith, the structure of which is an organic porous material comprising a continuous framework phase and a continuous pore phase, wherein the thickness of the continuous framework is 1 to 100 µm, the average diameter of the continuous pores is 1 to 1000 µm, and the total pore volume is 0.5 to 50 mL/g.

The thickness of the continuous framework of the monolithic anion exchanger in a dry state is 1 to 100 µm. When the thickness of the continuous framework of the monolithic anion exchanger is less than 1 µm, it is not preferable because there is not only a disadvantage such as a decrease in the anion exchange capacity per volume, but also a decrease in mechanical strength leading to a large deformation of the monolithic anion exchanger, especially when the liquid is passed through at a high flow rate. Furthermore, the contact efficiency between the reaction liquid and the monolithic anion exchanger is reduced, thereby reducing the catalytic activity, which is not preferable. On the other hand, when the thickness of the continuous framework of the monolithic anion exchanger is greater than 100 µm, it is not preferable because the framework becomes too thick and it takes more time for the substrate to be diffused, which reduces the catalytic activity. Note that the thickness of the continuous framework is determined by SEM observation.

The average diameter of the continuous pores of the monolithic anion exchanger in a dry state is 1 to 1000 μm. When the average diameter of the continuous pores of the monolithic anion exchanger is less than 1 μm, it is not preferable because the pressure loss upon passing water is high. On the other hand, when the average diameter of the continuous pores of the monolithic anion exchanger is greater than 1000 μm, it is not preferable because the contact between the liquid to be treated and the monolithic anion exchanger is insufficient, which reduces the removal performance. Note that the average diameter of the continuous pores of the monolithic anion exchanger in a dry state is measured by the mercury injection method and refers to the maximum value of the pore distribution curve obtained by the mercury injection method.

The total pore volume of the monolithic anion exchanger in a dry state is 0.5 to 50 mL/g. When the total pore volume of the monolithic anion exchanger is less than 0.5 mL/g, it is not preferable because the contact efficiency of the liquid to be treated is low, and furthermore, it is not preferable because the amount of permeate per unit cross sectional area is small, which reduces the throughput. On the other hand, when the total pore volume of the monolithic anion exchanger is greater than 50 mL/g, it is not preferable because the anion exchange capacity per volume is reduced, which reduces the removal performance. In addition, it is not preferable because the mechanical strength is decreased and the monolithic anion exchanger is largely deformed, especially when the liquid is passed through at a high speed, causing the pressure loss upon passing the liquid to rise rapidly. Note that the total pore volume is measured by the mercury injection method.

Exemplary structures of such a monolithic anion exchanger include the continuous bubble structures disclosed in Japanese Patent Laid-Open No. 2002-306976 and Japanese Patent Laid-Open No. 2009-62512, the co-continuous structure disclosed in Japanese Patent Laid-Open No. 2009-67982, the particle aggregated structure disclosed in Japanese Patent Laid-Open No. 2009-7550, and the particle composite structure disclosed in Japanese Patent Laid-Open No. 2009-108294.

The anion exchange capacity per volume of the monolithic anion exchanger in a water wet state is 0.2 to 1.0 mg equivalent/mL (water wet state). When the anion exchange capacity of the monolithic anion exchanger in a dry state is less than the range described above, it is not preferable because the amount of water to be treated before breakthrough is small and the frequency of replacement for the module is high. On the other hand, when it is greater than the range described above, it is not preferable because the pressure loss upon passing water is increased. Note that the anion exchange capacity of a porous material in which anion exchange groups are introduced only on the framework surface is at most 500 μg equivalent/g, although it is not possible to determine it in general, depending on the types of the porous material and anion exchange groups.

In the monolithic anion exchanger, the introduced anion exchange groups are uniformly distributed not only on the surface of the monolith, but also inside the framework of the monolith. The term "anion exchange groups are uniformly distributed" herein refers to the fact that the distribution of the anion exchange groups is such that they are uniformly distributed on the surface and inside the framework at least on the order of μm. The distribution of anion exchange groups can be easily confirmed by using EPMA. Also, when the anion exchange groups are uniformly distributed not only on the surface of the monolith but also inside the framework of the monolith, the physical properties and chemical properties of the surface and the inside can be made uniform, thus improving the resistance against swelling and shrinkage.

Examples of the anion exchange groups introduced into the monolithic anion exchanger include a quaternary ammonium group such as a trimethylammonium group, a triethylammonium group, a tributylammonium group, a dimethylhydroxyethylammonium group, a dimethylhydroxypropylammonium group, and a methyldihydroxyethylammonium group, a tertiary sulfonium group, and a phosphonium group.

In the monolithic anion exchanger, the material constituting the continuous framework is an organic polymer material having a crosslinked structure. Although the crosslinking density of the polymer material is not particularly limited, it is preferable to include 0.1 to 30 mol %, suitably 0.1 to 20 mol % of crosslinked structural units with respect to the entire constituent units that constitute the polymer material. When the crosslinked structural units are less than 0.1 mol %, it is not preferable because the mechanical strength is insufficient. On the other hand, when they are greater than 30 mol %, it is not preferable because the introduction of anion exchange groups may be difficult. There is no particular limitation on the type of the polymer material, and examples thereof include a crosslinked polymer, including, for example, an aromatic vinyl polymer such as polystyrene, poly($\alpha$-methylstyrene), polyvinyl toluene, polyvinylbenzyl chloride, polyvinyl biphenyl, and polyvinyl naphthalene; a polyolefin such as polyethylene and polypropylene; a poly(halogenated polyolefin) such as polyvinyl chloride and polytetrafluoroethylene; a nitrile-based polymer such as polyacrylonitrile; and a (meth)acrylic polymer such as polymethyl methacrylate, polyglycidyl methacrylate, and polyethyl acrylate. The polymers described above may be polymers obtained by copolymerizing a single vinyl monomer and a crosslinking agent, polymers obtained by polymerizing a plurality of vinyl monomers and a crosslinking agent, or a blend of two or more polymers. Among these organic polymer materials, crosslinked polymers of aromatic vinyl polymers are preferable because of the ease of forming a continuous structure, the ease of introducing anion exchange groups, the high mechanical strength, and the high stability against acids or alkalis, and in particular, styrene-divinylbenzene copolymers and vinylbenzyl chloride-divinylbenzene copolymers are preferable materials.

<Exemplary Embodiments of Monolithic Organic Porous Anion Exchanger>

Exemplary embodiments of the monolithic anion exchanger include the first monolithic anion exchanger and second monolithic anion exchanger, which will be shown below. In addition, exemplary embodiments of the monolith into which anion exchange groups are introduced include the first monolith and second monolith, which will be shown below.

<Description of First Monolith and First Monolithic Anion Exchanger>

The first monolithic anion exchanger is a monolithic anion exchanger having a continuous bubble structure with macropores linked to each other and common apertures (mesopores) with an average diameter of 1 to 1000 μm in a dry state within the walls of the macropores, having a total pore volume of 1 to 50 mL/g in a dry state, having anion exchange groups wherein the anion exchange groups are uniformly distributed, and having an anion exchange capacity per volume in a water wet state of 0.1 to 1.0 mg equivalent/mL (water wet state). In addition, the first monolith is a monolith before introducing the anion exchange groups, and is an organic porous material having a continuous bubble structure with macropores linked to each other and common apertures (mesopores) with an average diameter of 1 to 1000 μm in a dry state within the walls of the macropores, and having a total pore volume of 1 to 50 mL/g in a dry state.

Figure 3:
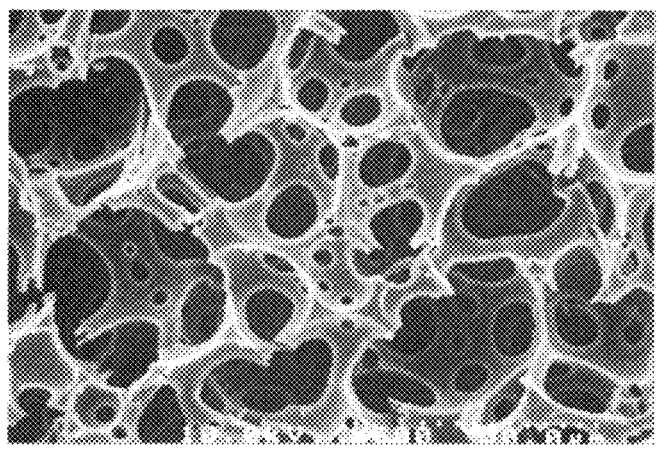
FIG. 3 is a scanning electron microscope (SEM) photograph of an exemplary embodiment of a first monolithic anion exchanger.

The first monolithic anion exchanger is a continuous macropore structural material in which bubble-like macropores overlap each other and these overlapping areas become common apertures (mesopores) with an average diameter of 1 to 1000 μm, preferably 10 to 200 μm, and particularly preferably 20 to 100 μm, in a dry state, the majority of which has an open pore structure. In the open pore structure, when the liquid flows, the flow channels are in the bubbles formed by the macropores and the mesopores. The number of overlaps between macropores is 1 to 12 for a single macropore and 3 to 10 for most. FIG. 3 shows a scanning electron microscope (SEM) photograph of an exemplary embodiment of the first monolithic anion exchanger. The first monolithic anion exchanger shown in FIG. 3 has a large number of bubble-like macropores, and is a continuous macropore structural material in which the bubble-like macropores overlap each other and these overlapping areas become common apertures (mesopores), the majority of which has an open pore structure. When the average diameter of the mesopores in a dry state is less than 1 μm, it is not preferable because the diffusibility of the liquid to be treated into the inside of the monolithic anion exchanger is low. On the other hand, when the average diameter of the mesopores in a dry state is greater than 1000 μm, it is not preferable because the contact between the liquid to be treated and the monolithic anion exchanger is insufficient, which reduces the removal performance. When the structure of the first monolithic anion exchanger is a continuous bubble structure as described above, groups of macropores and mesopores can be formed uniformly, and the pore volume and specific surface area can also be made significantly larger than those of particle aggregated porous materials as described in Japanese Patent Laid-Open No. 8-252579 and the like.

Note that, in the present invention, the average diameter of the apertures of the first monolith in a dry state and the average diameter of the apertures of the first monolithic anion exchanger in a dry state are measured by the mercury injection method and refer to the maximum value of the pore distribution curve obtained by the mercury injection method.

The total pore volume per weight of the first monolithic anion exchanger in a dry state is 1 to 50 mL/g, and suitably 2 to 30 mL/g. When the total pore volume is less than 1 mL/g, it is not preferable because the contact efficiency of the liquid to be treated is low, and furthermore, it is not preferable because the amount of permeate per unit cross sectional area is small, which reduces the throughput capacity. On the other hand, when the total pore volume is greater than 50 mL/g, it is not preferable because the mechanical strength is decreased and the monolithic anion exchanger is largely deformed, especially when the liquid is passed through at a high flow rate. Furthermore, the contact efficiency between the liquid to be treated and the monolithic anion exchanger is reduced, thereby also reducing the removal performance, which is not preferable. Since the total pore volume of conventional particulate porous anion exchange resins is 0.1 to 0.9 ml/g at most, those with a high pore volume of 1 to 50 ml/g and a high specific surface area, which have not been available in the past, can be used.

In the first monolithic anion exchanger, the material constituting the framework is an organic polymer material having a crosslinked structure. Although the crosslinking density of that polymer material is not particularly limited, it is preferable to include 0.3 to 10 mol %, suitably 0.3 to 5 mol % of crosslinked structural units with respect to the entire constituent units that constitute the polymer material. When the crosslinked structural units are less than 0.3 mol %, it is not preferable because the mechanical strength is insufficient. On the other hand, when they are greater than 10 mol %, it is not preferable because the introduction of anion exchange groups may be difficult.

There is no particular limitation on the type of the organic polymer material constituting the framework of the first monolithic anion exchanger, and examples thereof include a crosslinked polymer, including, for example, an aromatic vinyl polymer such as polystyrene, poly(α-methylstyrene), polyvinyl toluene, polyvinylbenzyl chloride, polyvinyl biphenyl, and polyvinyl naphthalene; a polyolefin such as polyethylene and polypropylene; a poly(halogenated polyolefin) such as polyvinyl chloride and polytetrafluoroethylene; a nitrile-based polymer such as polyacrylonitrile; and a (meth)acrylic polymer such as polymethyl methacrylate, polyglycidyl methacrylate, and polyethyl acrylate. The organic polymers described above may be polymers obtained by copolymerizing a single vinyl monomer and a crosslinking agent, polymers obtained by polymerizing a plurality of vinyl monomers and a crosslinking agent, or a blend of two or more polymers. Among these organic polymer materials, crosslinked polymers of aromatic vinyl polymers are preferable because of the ease of forming a continuous macropore structure, the ease of introducing anion exchange groups, the high mechanical strength, and the high stability against acids or alkalis, and in particular, styrene-divinylbenzene copolymers and vinylbenzyl chloride-divinylbenzene copolymers are preferable materials.

Examples of the anion exchange groups introduced into the first monolithic anion exchanger include a quaternary ammonium group such as a trimethylammonium group, a triethylammonium group, a tributylammonium group, a dimethylhydroxyethylammonium group, a dimethylhydroxypropylammonium group, and a methyldihydroxyethylammonium group, a tertiary sulfonium group, and a phosphonium group. The anion exchange groups introduced into the first monolithic anion exchanger are the same in the second monolithic anion exchanger.

In the first monolithic anion exchanger (the same applies to the second monolithic anion exchanger), the introduced anion exchange groups are uniformly distributed not only on the surface of the porous material, but also inside the framework of the porous material. The term "anion exchange groups are uniformly distributed" herein refers to the fact that the distribution of the anion exchange groups is such that they are uniformly distributed on the surface and inside the framework at least on the order of μm. The distribution of anion exchange groups can be confirmed by using EPMA. Also, when the anion exchange groups are uniformly distributed not only on the surface of the monolith but also inside the framework of the porous material, the physical properties and chemical properties of the surface and the inside can be made uniform, thus improving the resistance against swelling and shrinkage.

The anion exchange capacity per volume of the first monolithic anion exchanger in a water wet state is 0.1 to 1.0 mg equivalent/mL (water wet state). When the anion exchange capacity per volume in a water wet state is in the range described above, the removal performance is high and the service life is long. Note that the anion exchange capacity of a porous material in which anion exchange groups are introduced only on the surface is at most 500 μg equivalent/g, although it is not possible to determine it in general, depending on the types of the porous material and anion exchange groups.

<Method for Producing First Monolith and First Monolithic Anion Exchanger>

Although there is no limitation on the method for producing the first monolith, an example of the production method, according to the method described in Japanese Patent Laid-Open No. 2002-306976, is shown below. That is, the first monolith is obtained by mixing an oil soluble monomer without ion exchange groups, a surfactant, water and, if required, a polymerization initiator, to obtain a water in oil type emulsion, which is then polymerized to form the monolith. Such a method for producing the first monolith is preferable because of the ease of controlling the porous structure of the monolith.

The oil soluble monomer without ion exchange groups used in the production of the first monolith refers to a monomer that does not contain either cation exchange groups such as carboxylic acid groups or sulfonic acid groups or anion exchange groups such as quaternary ammonium groups, and that has low solubility in water and is lipophilic. Specific examples of such a monomer include styrene, α-methylstyrene, vinyl toluene, vinylbenzyl chloride, divinylbenzene, ethylene, propylene, isobutene, butadiene, isoprene, chloroprene, vinyl chloride, vinyl bromide, vinylidene chloride, tetrafluoroethylene, acrylonitrile, methacrylonitrile, vinyl acetate, methyl acrylate, ethyl acrylate, butyl acrylate, 2-ethylhexyl acrylate, trimethylolpropane triacrylate, butanediol diacrylate, methyl methacrylate, ethyl methacrylate, propyl methacrylate, butyl methacrylate, 2-ethylhexyl methacrylate, cyclohexyl methacrylate, benzyl methacrylate, glycidyl methacrylate, and ethylene glycol dimethacrylate. These monomers may be used alone as one kind, or may be used in combination of two or more kinds. However, in the present invention, it is preferable to select a crosslinkable monomer such as divinylbenzene or ethylene glycol dimethacrylate as at least one component of the oil soluble monomer and set the content thereof to 0.3 to 10 mol %, or suitably 0.3 to 5 mol %, of the entire oil soluble monomers in that anion exchange groups can be introduced quantitatively in the subsequent step and a practically sufficient mechanical strength can be ensured.

The surfactant used in the production of the first monolith is not particularly limited as long as it is capable of forming a water in oil type (W/O) emulsion when mixed with an oil soluble monomer without ion exchange groups and water. Examples of the surfactant that can be used include a non-cationic surfactant such as sorbitan monooleate, sorbitan monolaurate, sorbitan monopalmitate, sorbitan monostearate, sorbitan trioleate, polyoxyethylene nonylphenyl ether, polyoxyethylene stearyl ether, and polyoxyethylene sorbitan monooleate; a negative cationic surfactant such as potassium oleate, sodium dodecylbenzene sulfonate, sodium dioctyl sulfosuccinate; a positive cationic surfactant such as distearyl dimethyl ammonium chloride; and an amphoteric surfactant such as lauryl dimethyl betaine. These surfactants may be used alone as one kind or may be used in combination of two or more kinds. Note that a water in oil type emulsion refers to an emulsion in which the oil phase becomes a continuous phase and water droplets are dispersed therein. As for the amount of the surfactant to be added, it is difficult to say in general because it varies significantly depending on the type of oil soluble monomer and the size of the target emulsion particles (macropores), but it can be selected in the range of about 2 to 70% with respect to the total amount of the oil soluble monomer and the surfactant. Also, in order to control the bubble shape and size of the monolith, although it is not necessarily required, an alcohol such as methanol or stearyl alcohol; a carboxylic acid such as stearic acid; a hydrocarbon such as octane, dodecane, or toluene; or a cyclic ether such as tetrahydrofuran or dioxane may coexist in the system.

In addition, in the production of the first monolith, upon forming the monolith by polymerization, a compound that generates radicals by heat and light irradiation is suitably used as the polymerization initiator that is used if required. The polymerization initiator may be water soluble or oil soluble, and examples thereof include, for example, azobisisobutyronitrile, azobisdimethylvaleronitrile, azobiscyclohexanenitrile, azobiscyclohexanecarbonitrile, benzoyl peroxide, potassium persulfate, ammonium persulfate, hydrogen peroxide-ferrous chloride, sodium persulfate-sodium hydrogen sulfite, tetramethylthiuram disulfide. However, in some systems, polymerization proceeds only by heating or light irradiation without the addition of a polymerization initiator, and therefore the addition of a polymerization initiator is not necessary in such systems.

In the production of the first monolith, there is no limitation on the mixing method upon mixing an oil soluble monomer without ion exchange groups, a surfactant, water, and a polymerization initiator to form a water in oil type emulsion. For example, a method in which all components are mixed at once, or a method in which oil soluble components, including an oil soluble monomer, a surfactant, and an oil soluble polymerization initiator, and water soluble components, including water and a water soluble polymerization initiator, are separately dissolved to be uniform, and then these components are mixed together can be used. There is no particular limitation on the mixing apparatus for forming an emulsion, either. For example, an ordinary mixer, homogenizer, high pressure homogenizer, or so-called planetary stirring apparatus, which mixes the objects to be treated by placing them in a mixing vessel and allowing the vessel to rotate on its axis while making the vessel inclined and revolving around the revolution axis can be used, and an appropriate apparatus may be selected to obtain the target emulsion particle diameter. Also, there is no particular limitation on the mixing conditions, and the stirring speed and stirring time at which the target emulsion particle diameter can be obtained can be arbitrarily set. Among these mixing apparatuses, the planetary stirring apparatus is preferably used because it can uniformly produce water droplets in the W/O emulsion and its average diameter can be arbitrarily set over a wide range.

In the production of the first monolith, as for the polymerization conditions under which the water in oil type emulsion thus obtained is polymerized, a variety of conditions can be selected depending on the type of monomer and the initiator system. For example, when azobisisobutyronitrile, benzoyl peroxide, potassium persulfate, or the like is used as the polymerization initiator, heat polymerization may be performed at 30 to 100° C. for 1 to 48 hours in a sealed container under an inert atmosphere, and when hydrogen peroxide-ferrous chloride, sodium persulfate-sodium hydrogen sulfite, or the like is used as the initiator, polymerization may be performed at 0 to 30° C. for 1 to 48 hours in a sealed container under an inert atmosphere. After the completion of polymerization, the contents are taken out and soxhlet extracted with a solvent such as isopropanol to remove the unreacted monomer and residual surfactant, thereby obtaining the first monolith.

There is no particular limitation on the method for producing the first monolithic anion exchanger, and examples thereof include a method in which, instead of the monomer without ion exchange groups in the method for producing the first monolith described above, a monomer with anion exchange groups, such as a monomer formed by introducing anion exchange groups, such as monomethylammonium, dimethylammonium groups, and trimethylammonium groups into the oil soluble monomer without ion exchange groups described above, is polymerized to form a monolithic anion exchanger in one step, and a method in which a monomer without ion exchange groups is used and polymerized to form the first monolith and anion exchange groups are then introduced thereinto. Among these methods, the method in which a monomer without ion exchange groups is used and polymerized to form the first monolith and anion exchange groups are then introduced thereinto is preferable because the porous structure of the monolithic anion exchanger can be easily controlled and anion exchange groups can also be introduced quantitatively.

There is no particular limitation on the method for introducing anion exchange groups into the first monolith, and a known method such as polymer reaction or graft polymerization can be used. For example, examples of the method for introducing quaternary ammonium groups include: a method in which, when the monolith is a styrene-divinylbenzene copolymer or the like, chloromethyl groups are introduced using chloromethyl methyl ether or the like, and then the monolith is allowed to react with a tertiary amine; a method in which chloromethylstyrene and divinylbenzene are copolymerized to produce a monolith, which is then allowed to react with a tertiary amine; a method in which radical initiation groups or chain transfer groups are uniformly introduced into the monolith on the framework surface and inside the framework, and N, N, N-trimethylammonium ethyl acrylate or N, N, N-trimethylammonium propyl acrylamide is graft polymerized; and a method in which glycidyl methacrylate is graft polymerized in the same manner, and then quaternary ammonium groups are introduced by functional group transformation. Among these methods, as the method for introducing quaternary ammonium groups, the method in which chloromethyl groups are introduced into a styrene-divinylbenzene copolymer using chloromethyl methyl ether or the like, and then the monolith is allowed to react with a tertiary amine, or the method in which chloromethylstyrene and divinylbenzene are copolymerized to produce a monolith, which is then allowed to react with a tertiary amine is preferable in that ion exchange groups can be introduced uniformly and quantitatively. Note that examples of the ion exchange groups to be introduced include a quaternary ammonium group such as a trimethylammonium group, a triethylammonium group, a tributylammonium group, a dimethylhydroxyethylammonium group, a dimethylhydroxypropylammonium group, and a methyldihydroxyethylammonium group, a tertiary sulfonium group, and a phosphonium group.

<Description of Second Monolith and Second Monolithic Anion Exchanger>

The second monolithic anion exchanger is a co-continuous structural material formed of a three dimensionally continuous framework comprising an aromatic vinyl polymer containing 0.1 to 5.0 mol % of crosslinked structural units among the entire constituent units, with an average thickness of 1 to 60 μm in a dry state, and three dimensionally continuous pores in the framework with an average diameter of 10 to 200 μm in a dry state; has a total pore volume of 0.5 to 10 mL/g in a dry state; has anion exchange groups; has an anion exchange capacity per volume in a water wet state of 0.2 to 1.0 mg equivalent/mL (water wet state); and is a monolithic anion exchanger in which the anion exchange groups are uniformly distributed in the organic porous anion exchanger. In addition, the second monolith is a monolith before introducing the anion exchange groups, and is a co-continuous structural material formed of a three dimensionally continuous framework comprising an aromatic vinyl polymer containing 0.1 to 5.0 mol % of crosslinked structural units among the entire constituent units, with an average thickness of 1 to 60 μm in a dry state, and three dimensionally continuous pores in the framework with an average diameter of 10 to 200 μm in a dry state; and is an organic porous material with a total pore volume of 0.5 to 10 mL/g in a dry state.

Figure 4:
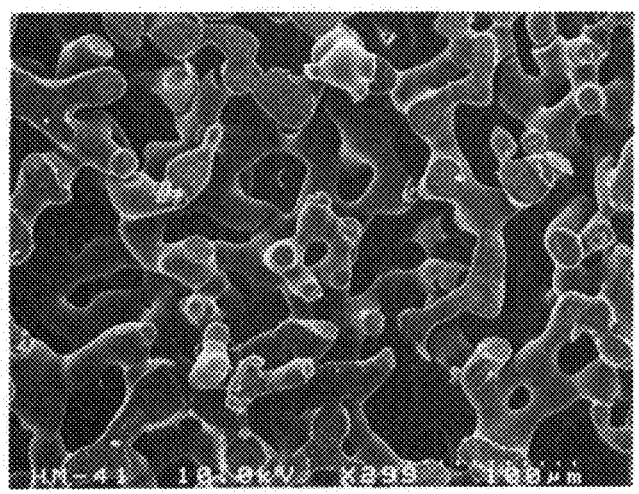
FIG. 4 is a SEM photograph of an exemplary embodiment of a second monolithic anion exchanger.
Figure 5:
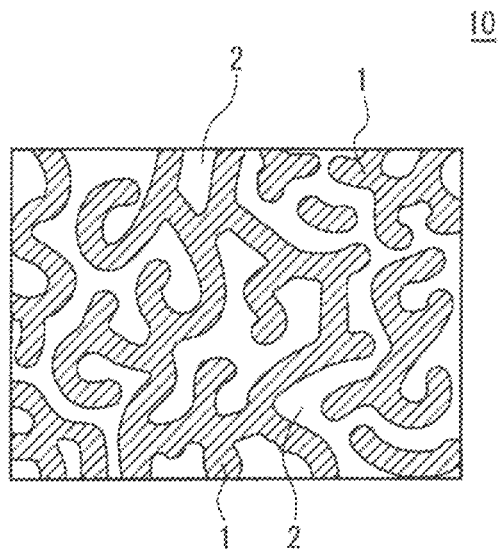
FIG. 5 is a schematic diagram of the co-continuous structure of the second monolithic anion exchanger.

The second monolithic anion exchanger is a co-continuous structural material formed of a three dimensionally continuous framework with an average thickness of 1 to 60 μm, preferably 3 to 58 μm, in a dry state, and three dimensionally continuous pores in the framework with an average diameter of 10 to 200 μm, preferably 15 to 180 μm, and particularly preferably 20 to 150 μm, in a dry state. FIG. 4 shows a SEM photograph of an exemplary embodiment of the second monolithic anion exchanger, and FIG. 5 illustrates a schematic diagram of the co-continuous structure of the second monolithic anion exchanger. The co-continuous structure is a structure 10 in which a continuous framework phase 1 and a continuous pore phase 2 are intertwined and are both three dimensionally continuous, as illustrated in the schematic diagram of FIG. 4. These continuous pores 2 have a higher degree of continuity of pores and have less deviation in their size than conventional continuous bubble monoliths and particle aggregated monoliths. In addition, the mechanical strength is high due to the thick framework.

When the average diameter of the three dimensionally continuous pores in a dry state is less than 10 μm, it is not preferable because the liquid to be treated is difficult to be diffused. On the other hand, when it is greater than 200 μm, it is not preferable because the contact between the liquid to be treated and the monolithic anion exchanger is insufficient, which results in insufficient removal performance. Also, when the average thickness of the framework is less than 1 μm in the dry state, it is not preferable because the anion exchange capacity is low and the mechanical strength is also low. Furthermore, the contact efficiency between the reaction liquid and the monolithic anion exchanger is reduced, thereby reducing the removal performance, which is not preferable. On the other hand, when the thickness of the framework is greater than 60 μm, it is not preferable because the framework becomes too thick and diffusion of the liquid to be treated becomes nonuniform.

The average diameter of the apertures of the second monolith in a dry state, the average diameter of the apertures of the second monolithic anion exchanger in a dry state, and the average diameter of the apertures of a second monolithic intermediate (2) in a dry state, which is obtained in a step I of the production of the second monolith, which will be mentioned later, are determined by the mercury injection method and refer to the maximum value of the pore distribution curve obtained by the mercury injection method. Also, the average thickness of the framework of the second monolithic anion exchanger in a dry state is determined by SEM observation of the second monolithic anion exchanger in a dry state. Specifically, SEM observations of the second monolithic anion exchanger in a dry state are performed at least three times, and the thickness of the framework in the obtained images is measured, and the average value thereof is defined as the average thickness. Note that the framework is rod-shaped and has a circular cross sectional shape, but it may also include one with a different diameter cross section, such as an oval cross sectional shape. In this case, the thickness is the average of the short and long diameters.

In addition, the total pore volume per weight of the second monolithic anion exchanger in a dry state is 0.5 to 10 mL/g. When the total pore volume is less than 0.5 mL/g, it is not preferable because the contact efficiency of the substrate or the solvent is low, and furthermore, it is not preferable because the amount of permeate per unit cross sectional area is small, which reduces the throughput. On the other hand, when the total pore volume is greater than 10 ml/g, the contact efficiency between the liquid to be treated and the monolithic anion exchanger is reduced, thereby reducing the removal performance, which is not preferable. When the size and total pore volume of the three dimensionally continuous pores are within the ranges described above, the contact with the liquid to be treated is extremely uniform and the contact area is large.

In the second monolithic anion exchanger, the material constituting the framework is an aromatic vinyl polymer including 0.1 to 5 mol %, preferably 0.5 to 3.0 mol % of crosslinked structural units among the entire constituent units, and is hydrophobic. When the crosslinked structural units are less than 0.1 mol %, it is not preferable because the mechanical strength is insufficient. On the other hand, when they are greater than 5 mol %, the structure of the porous material easily deviates from the co-continuous structure. There is no particular limitation on the type of the aromatic vinyl polymer, and examples thereof include, for example, polystyrene, poly($\alpha$-methylstyrene), polyvinyl toluene, polyvinylbenzyl chloride, polyvinyl biphenyl, and polyvinyl naphthalene. The polymers described above may be polymers obtained by copolymerizing a single vinyl monomer and a crosslinking agent, polymers obtained by polymerizing a plurality of vinyl monomers and a crosslinking agent, or a blend of two or more polymers. Among these organic polymer materials, styrene-divinylbenzene copolymers and vinylbenzyl chloride-divinylbenzene copolymers are preferable because of the ease of forming a co-continuous structure, the ease of introducing anion exchange groups, the high mechanical strength, and the high stability against acids or alkalis.

The anion exchange groups introduced into the second monolithic anion exchanger are the same as the anion exchange groups introduced into the first monolithic anion exchanger.

In the second monolithic anion exchanger, the introduced anion exchange groups are uniformly distributed not only on the surface of the porous material, but also inside the framework of the porous material.

The second monolithic anion exchanger has an anion exchange capacity per volume in a water wet state of 0.2 to 1.0 mg equivalent/mL (water wet state). The second monolithic anion exchanger has a high degree of continuity and uniformity of three dimensionally continuous pores, which allows for uniform diffusion of the substrate and solvent. Therefore, the reaction proceeds quickly. When the anion exchange capacity is in the range described above, the removal performance is high and the service life is long.

<Method for Producing Second Monolith and Second Monolithic Anion Exchanger>

The second monolith is obtained by carrying out the following steps: stirring a mixture of an oil soluble monomer without ion exchange groups, a surfactant, and water, thereby preparing a water in oil type emulsion, and then polymerizing the water in oil type emulsion to obtain a monolithic organic porous intermediate (hereinafter, also referred to as a monolithic intermediate (2)) having a continuous macropore structure with a total pore volume of greater than 16 mL/g and not more than 30 mL/g (a step I); preparing a mixture formed of an aromatic vinyl monomer, a crosslinking agent at 0.3 to 5 mol % among the entire oil soluble monomers having at least two or more vinyl groups in one molecule, an organic solvent that dissolves the aromatic vinyl monomer and the crosslinking agent, but does not dissolve a polymer produced by polymerization of the aromatic vinyl monomer, and a polymerization initiator (a step II); polymerizing the mixture obtained in the step II while leaving it to stand still and in the presence of the monolithic intermediate (2) obtained in the step I, thereby obtaining a second monolith, which is an organic porous material with a co-continuous structure (a step III).

In the step I according to the method for producing the second monolith, the step I of obtaining the monolithic intermediate (2) may be carried out in accordance with the method described in Japanese Patent Laid-Open No. 2002-306976.

That is, in the step I according to the method for producing the second monolith, examples of the oil soluble monomer without ion exchange groups include, for example, a monomer that does not contain ion exchange groups such as carboxylic acid groups, sulfonic acid groups, tertiary amino groups, and quaternary ammonium groups, and that has low solubility in water and is lipophilic. Specific examples of such a monomer include an aromatic vinyl monomer such as styrene, $\alpha$-methylstyrene, vinyl toluene, vinylbenzyl chloride, vinyl biphenyl, and vinyl naphthalene; an $\alpha$-olefin such as ethylene, propylene, 1-butene, and isobutene; a diene-based monomer such as butadiene, isoprene, and chloroprene; a halogenated olefin such as vinyl chloride, vinyl bromide, vinylidene chloride, and tetrafluoroethylene; a nitrile-based monomer such as acrylonitrile and methacrylonitrile; a vinyl ester such as vinyl acetate and vinyl propionate; and a (meth)acrylic monomer such as methyl acrylate, ethyl acrylate, butyl acrylate, 2-ethylhexyl acrylate, methyl methacrylate, ethyl methacrylate, propyl methacrylate, butyl methacrylate, 2-ethylhexyl methacrylate, cyclohexyl methacrylate, benzyl methacrylate, and glycidyl methacrylate. Among these monomers, the aromatic vinyl monomer is suitable, and examples thereof include styrene, $\alpha$-methylstyrene, vinyl toluene, vinylbenzyl chloride, and divinylbenzene. These monomers may be used alone as one kind, or may be used in combination of two or more kinds. However, it is preferable to select a crosslinkable monomer such as divinylbenzene or ethylene glycol dimethacrylate as at least one component of the oil soluble monomer and set the content thereof to 0.3 to 5 mol %, or suitably 0.3 to 3 mol %, of the entire oil soluble monomers because it is advantageous for the formation of a co-continuous structure.

The surfactant used in the step I according to the method for producing the second monolith is not particularly limited as long as it is capable of forming a water in oil type (W/O) emulsion when mixed with an oil soluble monomer without anion exchange groups and water. Examples of the surfactant that can be used include a non-cationic surfactant such as sorbitan monooleate, sorbitan monolaurate, sorbitan monopalmitate, sorbitan monostearate, sorbitan trioleate, polyoxyethylene nonylphenyl ether, polyoxyethylene stearyl ether, and polyoxyethylene sorbitan monooleate; a negative cationic surfactant such as potassium oleate, sodium dodecylbenzene sulfonate, sodium dioctyl sulfosuccinate; a positive cationic surfactant such as distearyl dimethyl ammonium chloride; and an amphoteric surfactant such as lauryl dimethyl betaine. These surfactants may be used alone as one kind or may be used in combination of two or more kinds. Note that a water in oil type emulsion refers to an emulsion in which the oil phase becomes a continuous phase and water droplets are dispersed therein. As for the amount of the surfactant to be added, it is difficult to say in general because it varies significantly depending on the type of oil soluble monomer and the size of the target emulsion particles (macropores), but it can be selected in the range of about 2 to 70% with respect to the total amount of the oil soluble monomer and the surfactant.

In addition, in the step I according to the method for producing the second monolith, a polymerization initiator may be used, if required, upon forming the water in oil type emulsion. As the polymerization initiator, a compound that generates radicals by heat or light irradiation is suitably used. The polymerization initiator may be water soluble or oil soluble, and examples thereof include, for example, 2,2'-azobis(isobutyronitrile), 2,2'-azobis(2,4-dimethylvaleronitrile), 2,2'-azobis(2-methylbutyronitrile), 2,2'-azobis(4-methoxy-2,4-dimethylvaleronitrile), dimethyl 2,2'-azobis (isobutyrate), 4,4'-azobis(4-cyanovaleric acid), 1,1'-azobis (cyclohexane-1-carbonitrile), benzoyl peroxide, lauroyl peroxide, potassium persulfate, ammonium persulfate, tetramethylthiuram disulfide, hydrogen peroxide-ferrous chloride, and sodium persulfate-sodium hydrogen sulfite.

In the step I according to the method for producing the second monolith, there is no limitation on the mixing method upon mixing an oil soluble monomer without ion exchange groups, a surfactant, water, and a polymerization initiator to form a water in oil type emulsion. For example, a method in which all components are mixed at once, or a method in which oil soluble components, including an oil soluble monomer, a surfactant, and an oil soluble polymerization initiator, and water soluble components, including water and a water soluble polymerization initiator, are separately dissolved to be uniform, and then these components are mixed together can be used. There is no particular limitation on the mixing apparatus for forming an emulsion, either. For example, an ordinary mixer, homogenizer, or high pressure homogenizer can be used, and an appropriate apparatus may be selected to obtain the target emulsion particle diameter. Also, there is no particular limitation on the mixing conditions, and the stirring speed and stirring time at which the target emulsion particle diameter can be obtained can be arbitrarily set.

The monolithic intermediate (2) obtained in the step I according to the method for producing the second monolith is an organic polymer material having a crosslinked structure, and is suitably an aromatic vinyl polymer. Although the crosslinking density of that polymer material is not particularly limited, it is preferable to include 0.1 to 5 mol %, preferably 0.3 to 3 mol % of crosslinked structural units with respect to the entire constituent units that constitute the polymer material. When the crosslinked structural units are less than 0.3 mol %, it is not preferable because the mechanical strength is insufficient. On the other hand, when they are greater than 5 mol %, it is not preferable because the structure of the monolith easily deviates from the co-continuous structure. In particular, when the total pore volume is 16 to 20 ml/g, it is preferable that the crosslinked structural units should be less than 3 mol % in order to form a co-continuous structure.

In the step I according to the method for producing the second monolith, examples of the type of polymer material of the monolithic intermediate (2) include those that are the same as the polymer material of the first monolith.

Figure 6:
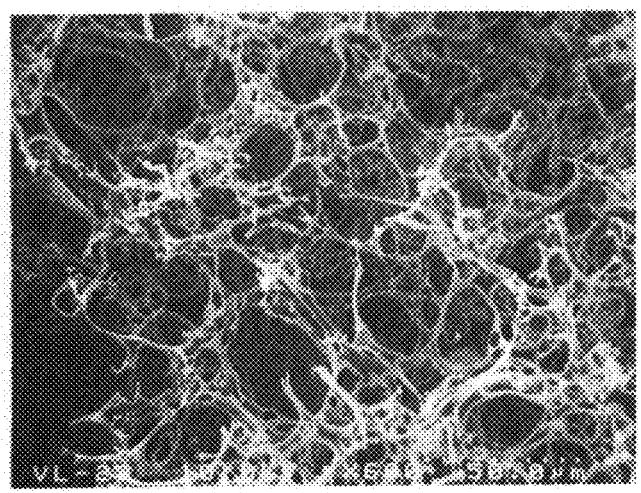
FIG. 6 is a SEM photograph of an exemplary embodiment of a monolithic intermediate (2).

The total pore volume per weight of the monolithic intermediate (2) in a dry state, obtained in the step I according to the method for producing the second monolith, is greater than 16 mL/g and not more than 30 mL/g, and suitably greater than 16 mL/g and not more than 25 mL/g. That is, although this monolithic intermediate (2) basically has a continuous macropore structure, its apertures (mesopores), which are the overlapping portions of macropores with each other, are significantly large, and therefore the framework constituting the monolithic structure has a structure that is very close to a two dimensional wall surface to a one dimensional rod-like framework. FIG. 6 shows a SEM photograph of an exemplary embodiment of the monolithic intermediate (2), which has a near rod-like framework. When this is allowed to coexist in the polymerization system, a porous material with a co-continuous structure is formed using the structure of the monolithic intermediate (2) as a mold. When the total pore volume is too small, it is not preferable because the structure of the monolith obtained after the polymerization of the vinyl monomer changes from a co-continuous structure to a continuous macropore structure. On the other hand, when the total pore volume is too large, it is not preferable because the mechanical strength of the monolith obtained after the polymerization of the vinyl monomer is reduced, or when anion exchange groups are introduced, the anion exchange capacity per volume is reduced. To make the total pore volume of the monolithic intermediate (2) within the range described above, the ratio of monomer to water should be generally 1:20 to 1:40.

In addition, for the monolithic intermediate (2) obtained in the step I according to the method for producing the second monolith, the average diameter of apertures (mesopores), which are the overlapping portions of macropores with each other, in a dry state is 5 to 100 μm. When the average diameter of apertures in a dry state is less than 5 μm, it is not preferable because the aperture diameter of the monolith obtained after the polymerization of the vinyl monomer is small and the pressure loss upon fluid permeation is large. On the other hand, when it is greater than 100 μm, it is not preferable because the aperture diameter of the monolith obtained after the polymerization of the vinyl monomer is too large and the contact between the liquid to be treated and the monolithic anion exchanger is insufficient, resulting in a reduction in the removal performance. It is suitable for the monolithic intermediate (2) to have a uniform structure in which the sizes of the macropores and the diameters of the apertures are uniform, but it is not limited to this, and may be dotted with nonuniform macropores that are larger than the size of the uniform macropores in the uniform structure.

The step II according to the method for producing the second monolith is a step of preparing a mixture formed of an aromatic vinyl monomer, a crosslinking agent at 0.3 to 5 mol % among the entire oil soluble monomers having at least two or more vinyl groups in one molecule, an organic solvent that dissolves the aromatic vinyl monomer and the crosslinking agent, but does not dissolve a polymer produced by polymerization of the aromatic vinyl monomer, and a polymerization initiator. Note that there is no order for the step I and the step II, and the step II may be performed after the step I or the step I may be performed after the step II.

As for the aromatic vinyl monomer used in the step II according to the method for producing the second monolith, there is no particular limitation as long as it contains a polymerizable vinyl group in the molecule and is lipophilic aromatic vinyl monomer with high solubility in an organic solvent. However, it is preferable to select a vinyl monomer that produces a polymer material of the same type as or similar to the monolithic intermediate (2) coexisting in the polymerization system described above. Specific examples of such a vinyl monomer include styrene, α-methylstyrene, vinyl toluene, vinylbenzyl chloride, vinyl biphenyl, and vinyl naphthalene. These monomers may be used alone as one kind, or may be used in combination of two or more kinds. An aromatic vinyl monomer that is suitably used is styrene, vinylbenzyl chloride, or the like.

The amount to be added of the aromatic vinyl monomer used in the step II according to the method for producing the second monolith is 5 to 50 times, preferably 5 to 40 times by weight, with respect to the monolithic intermediate (2) coexisting at the time of polymerization. When the amount of the aromatic vinyl monomer to be added is less than 5 times that of the monolithic intermediate (2), it is not preferable because the rod-like framework cannot be made thicker and the anion exchange capacity per volume after the introduction of anion exchange groups is small when the anion exchange groups are introduced. On the other hand, when the amount of the aromatic vinyl monomer to be added is greater than 50 times, it is not preferable because the diameter of the continuous pores is small and the pressure loss upon passing the liquid is large.

As the crosslinking agent used in the step II according to the method for producing the second monolith, those containing at least two polymerizable vinyl groups in the molecule and having a high solubility in an organic solvent are suitably used. Specific examples of the crosslinking agent include divinylbenzene, divinyl naphthalene, divinyl biphenyl, ethylene glycol dimethacrylate, trimethylolpropane triacrylate, and butanediol diacrylate. These crosslinking agents may be used alone as one kind, or may be used in combination of two or more kinds. A preferable crosslinking agent is an aromatic polyvinyl compound such as divinylbenzene, divinyl naphthalene, and divinyl biphenyl because of its high mechanical strength and stability against hydrolysis. The amount of the crosslinking agent to be used is 0.3 to 5 mol %, in particular 0.3 to 3 mol %, of the total amount of the vinyl monomer and crosslinking agent (the entire oil soluble monomers). When the amount of the crosslinking agent to be used is less than 0.3 mol %, it is not preferable because the mechanical strength of the monolith is insufficient. On the other hand, when it is too large, it is not preferable because quantitative introduction of anion exchange groups may be difficult when the anion exchange groups are introduced. Note that it is preferable to use the crosslinking agent described above in an amount to be used such that the crosslinking density of the vinyl monomer and the crosslinking agent is approximately equal to that of the monolithic intermediate (2) coexisting upon the polymerization of the vinyl monomer/crosslinking agent. When both are used in amounts that are too far apart, a deviation in the crosslinking density distribution occurs in the produced monolith, and when anion exchange groups are introduced, cracks are likely to be generated upon the introduction reaction of the anion exchange groups.

The organic solvent used in the step II according to the method for producing the second monolith is an organic solvent that dissolves the aromatic vinyl monomer and the crosslinking agent, but does not dissolve a polymer produced by polymerization of the aromatic vinyl monomer. In other words, it is a poor solvent for a polymer produced by polymerization of the aromatic vinyl monomer. Since the organic solvent greatly varies depending on the type of the aromatic vinyl monomer, it is difficult to specifically recite general examples, but for example, when the aromatic vinyl monomer is styrene, examples of the organic solvent include an alcohol such as methanol, ethanol, propanol, butanol, hexanol, cyclohexanol, octanol, 2-ethylhexanol, decanol, dodecanol, propylene glycol, and tetramethylene glycol; a chain (poly) ether such as diethyl ether, butyl cellosolve, polyethylene glycol, polypropylene glycol, and polytetramethylene glycol; a chain saturated hydrocarbon such as hexane, heptane, octane, isooctane, decane, and dodecane; an ester such as ethyl acetate, isopropyl acetate, cellosolve acetate, and ethyl propionate. Also, even a good solvent for polystyrene, such as dioxane, THF, or toluene, can be used as the organic solvent when it is used together with the poor solvents described above and the amount thereof to be used is small. It is preferable to use these organic solvents in an amount to be used such that the concentration of the above aromatic vinyl monomer is 30 to 80% by weight. When the amount of the organic solvent to be used departs from the range described above and the concentration of the aromatic vinyl monomer is less than 30% by weight, it is not preferable because the polymerization rate is reduced or the monolithic structure after polymerization departs from the range of the second monolith. On the other hand, when the concentration of the aromatic vinyl monomer is greater than 80% by weight, it is not preferable because the polymerization may run out of control.

As the polymerization initiator used in the step II according to the method for producing the second monolith, a compound that generates radicals by heat or light irradiation is suitably used. It is preferable that the polymerization initiator should be oil soluble. Specific examples of the polymerization initiator include 2,2'-azobis(isobutyronitrile), 2,2'-azobis(2,4-dimethylvaleronitrile), 2,2'-azobis(2-methylbutyronitrile), 2,2'-azobis(4-methoxy-2,4-dimethylvaleronitrile), dimethyl 2,2'-azobis(isobutyrate), 4,4'-azobis(4-cyanovaleric acid), 1,1'-azobis(cyclohexane-1-carbonitrile), benzoyl peroxide, lauroyl peroxide, potassium persulfate, ammonium persulfate, and tetramethylthiuram disulfide. Although the amount of the polymerization initiator to be used varies greatly depending on the type of monomer, polymerization temperature, and the like, it can be used in a range of about 0.01 to 5% with respect to the total amount of the vinyl monomer and the crosslinking agent.

The step III according to the method for producing the second monolith is a step of polymerizing the mixture obtained in the step II while leaving it to stand still and in the presence of the monolithic intermediate (2) obtained in the step I, thereby changing the continuous macropore structure of the monolithic intermediate (2) to a co-continuous structure, obtaining a second monolith, which is a monolith with a co-continuous structure. The monolithic intermediate (2) used in the step III plays an extremely important role in creating a monolith with the structure of the present invention. As disclosed in Japanese Translation of PCT International Application Publication No. 1995-501140 and the like, static polymerization of the vinyl monomer and the crosslinking agent in a certain organic solvent in the absence of the monolithic intermediate (2) yields a particle aggregated type monolithic organic porous material. In contrast, when a monolithic intermediate (2) with a particular continuous macropore structure is present in the above polymerization system, as in the case of producing the second monolith, the structure of the monolith after polymerization is changed dramatically, the particle aggregated structure disappears, and the second monolith with the co-continuous structure mentioned above is obtained. Although the reason for this has not been elucidated in detail, it is thought that, when the monolithic intermediate (2) is not present, the particle aggregated structure is formed by the precipitation and sedimentation of the crosslinked polymer produced by the polymerization in a particle form, whereas when a porous material (intermediate) with a large total pore volume is present in the polymerization system, the vinyl monomer and the crosslinking agent are adsorbed or distributed from the liquid phase to the framework part of the porous material, polymerization proceeds in the porous material, and the framework constituting the monolithic structure is changed from a two dimensional wall surface to a one dimensional rod-like framework, thereby forming a second monolith having a co-continuous structure.

In the method for producing the second monolith, there is no particular limitation on the inner volume of the reaction vessel as long as it is large enough to allow the monolithic intermediate (2) to exist in the reaction vessel, and when the monolithic intermediate (2) is placed in the reaction vessel, a gap may be created around the monolith in a plane view or the monolithic intermediate (2) may be placed in the reaction vessel with no gap, either of which is fine. Among the above, a case is efficient in which a monolith with a thick framework after polymerization is placed in the reaction vessel with no gap without receiving pressure from the inner wall of the vessel, which does not cause distortion of the monolith and does not waste reaction raw materials and the like. Note that, even when the inner volume of the reaction vessel is large and there are gaps around the monolith after polymerization, the vinyl monomer and the crosslinking agent are adsorbed and distributed to the monolithic intermediate (2), and therefore, no particle aggregated structure is produced in the part of gaps in the reaction vessel.

In the step III according to the method for producing the second monolith, the monolithic intermediate (2) is placed in the reaction vessel in a state of being impregnated with the mixture (solution). As for the compounding ratio between the mixture obtained in the step II and the monolithic intermediate (2), it is suitable that they should be compounded such that the amount of the vinyl monomer to be added is 3 to 50 times, preferably 4 to 40 times by weight with respect to the monolithic intermediate (2), as mentioned above. By doing so, a second monolith with a thick framework while having a moderate aperture diameter can be obtained. In the reaction vessel, the vinyl monomer and crosslinking agent in the mixture are adsorbed and distributed to the framework of the monolithic intermediate that is left to stand still, and polymerization proceeds in the framework of the monolithic intermediate (2).

In the step III according to the method for producing the second monolith, the monolithic intermediate (2) is placed in the reaction vessel in a state of being impregnated with the mixture (solution). As for the compounding ratio between the mixture obtained in the step II and the monolithic intermediate (2), it is suitable that they should be compounded such that the amount of the aromatic vinyl monomer to be added is 5 to 50 times, preferably 5 to 40 times by weight with respect to the monolithic intermediate (2), as mentioned above. By doing so, a second monolith with a co-continuous structure in which moderately sized pores are three dimensionally continuous and the thick framework is also three dimensionally continuous can be obtained. In the reaction vessel, the aromatic vinyl monomer and crosslinking agent in the mixture are adsorbed and distributed to the framework of the monolithic intermediate (2) that is left to stand still, and polymerization proceeds in the framework of the monolithic intermediate (2).

As for the polymerization conditions in the step III according to the method for producing the second monolith, a variety of conditions are selected depending on the type of monomer and the type of initiator. For example, when 2,2'-azobis(isobutyronitrile), 2,2'-azobis(2,4-dimethylvaleronitrile), benzoyl peroxide, lauroyl peroxide, potassium persulfate, or the like is used as the initiator, heat polymerization may be performed at 30 to 100° C. for 1 to 48 hours in a sealed container under an inert atmosphere. By the heat polymerization, the vinyl monomer and crosslinking agent that have been adsorbed and distributed to the framework of the monolithic intermediate (2) are polymerized in the framework, making the framework thicker. After the completion of polymerization, the contents are taken out and extracted with a solvent such as acetone for the purpose of removing the unreacted vinyl monomer and the organic solvent, thereby obtaining the second monolith.

The second monolithic anion exchanger is obtained by performing a step IV to introduce anion exchange groups into the second monolith obtained in the step III.

The method for introducing anion exchange groups into the second monolith is the same as the method for introducing anion exchange groups into the first monolith.

The second monolith and the second monolithic anion exchanger have high mechanical strength due to their thick framework even though the size of the three dimensionally continuous pores is significantly large. In addition, since the second monolithic anion exchanger has a thick framework, the anion exchange capacity per volume in a water wet state can be increased, and furthermore, the liquid to be treated can be kept flowing at a low pressure and high flow rate for a long period of time.

Also, the monolithic cation exchanger differs from the monolithic anion exchanger in that the ion exchange groups introduced into the monolith are cation exchange groups rather than anion exchange groups, but is otherwise similar. Therefore, for the monolithic cation exchanger, anion should be read as cation in the above description for the monolithic anion exchanger. In the following, for the monolithic cation exchanger, some points that are different from the monolithic anion exchanger will be explained.

Examples of the cation exchange groups introduced into the monolithic cation exchanger include a sulfonic acid group, a carboxyl group, an iminodiacetic acid group, a phosphoric acid group, and a phosphate ester group. In addition, examples of the cation exchange groups introduced into the first monolithic cation exchanger include a carboxylic acid group, an iminodiacetic acid group, a sulfonic acid group, a phosphoric acid group, and a phosphate ester group. The cation exchange groups introduced into the first monolithic cation exchanger are the same in the second monolithic cation exchanger.

In addition, as for the method for introducing cation exchange groups, for example, the method for introducing sulfonic acid groups into the monolith, examples thereof include: a method in which, when the monolith is a styrene-divinylbenzene copolymer or the like, chlorosulfuric acid, concentrated sulfuric acid, or fuming sulfuric acid is used for sulfonation; a method in which radical initiation groups or chain transfer groups are uniformly introduced into the monolith on the framework surface and inside the framework, and sodium styrenesulfonate or acrylamido-2-methylpropanesulfonic acid is graft polymerized; and a method in which glycidyl methacrylate is graft polymerized in the same manner, and then sulfonic acid groups are introduced by functional group transformation. Among these methods, the method in which chlorosulfuric acid is used to introduce sulfonic acid into a styrene-divinylbenzene copolymer is preferable in that cation exchange groups can be introduced uniformly and quantitatively. Note that examples of the cation exchange groups to be introduced include a cation exchange group such as a carboxylic acid group, an iminodiacetic acid group, a sulfonic acid group, a phosphoric acid group, and a phosphate ester group.

In the monolithic organic porous cation exchanger and the monolithic organic porous anion exchanger, as compared to the porous membranes and ion exchange resins that are used in other methods for analyzing the content of ionic impurities, the captured ionic impurity elements are more easily eluted by the eluent. Therefore, the method for analyzing the metal impurity content of the present invention (the method for analyzing the metal impurity content of the first embodiment of the present invention, the method for analyzing the metal impurity content of the second embodiment of the present invention, and the method for analyzing the metal impurity content of the third embodiment of the present invention are collectively referred to as the method for analyzing the metal impurity content of the present invention) can lower the acid concentration of the eluent, and thus the lower limit of quantification becomes lower.

In the monolithic organic porous cation exchanger and the monolithic organic porous anion exchanger, as compared to the porous membranes and ion exchange resins that are used in other methods for analyzing the metal impurity content, the captured metal impurity elements are more easily eluted by the eluent. Therefore, the method for analyzing the metal impurity content of the present invention can reduce the time required for the elution step, thus reducing the analysis time.

In the monolithic organic porous cation exchanger and the monolithic organic porous anion exchanger, as compared to the porous membranes and ion exchange resins that are used in other methods for analyzing the metal impurity content, the passing speed of the water to be analyzed can be made higher. Therefore, the method for analyzing the metal impurity content of the present invention can reduce the time required for the impurity capturing step, thus reducing the analysis time.

And, when the metal impurity content in the water to be analyzed is very low, for example, 1 ppt or less, a large amount of water to be analyzed needs to be passed through the adsorbent. In the method for analyzing the metal impurity content of the present invention, the amount of the eluent to be used can be reduced since the captured metal impurity elements are easily eluted by the eluent, and thus the passing amount of the water to be analyzed into the monolithic porous ion exchanger can be reduced. Moreover, since the passing speed of the water to be analyzed can be increased, a large amount of liquid can be passed through the monolithic porous ion exchanger in a short period of time, and thus the time required for the capturing step in the analysis can be made very short. In the method for analyzing the metal impurity content of the present invention, when the metal impurity content in the water to be analyzed is very low, the content of each metal impurity in the water to be analyzed is, for example, 1.000 ppt or less, or 0.001 to 1.000 ppt, or 0.001 to 0.100 ppt. Also, in this case, the pressure coefficient in the capturing step of the method for analyzing the metal impurity content of the present invention is preferably 0.1 to 10.0 L/min./MPa, and particularly preferably 2.0 to 10.0 L/min./MPa.

In addition, the monolithic organic porous anion exchanger exerts excellent capturing performance for the capture of B, As, Al, Ti, Cr, Fe, Cu, Zn, Sn, V, Ga, and Pb, in particular for the capture of B or As in the water to be analyzed. Therefore, the method for analyzing the metal impurity content of the first embodiment of the present invention and the method for analyzing the metal impurity content of the third embodiment of the present invention are excellent in their analytical performance for the content of B, As, Al, Ti, Cr, Fe, Cu, Zn, Sn, V, Ga, and Pb, in particular B or As, in the analysis subject.

In the method for analyzing the metal impurity elements of the third embodiment of the present invention, the same water to be analyzed is passed through both the monolithic organic porous anion exchanger and the monolithic organic porous cation exchanger, and the same eluent is passed through both the monolithic organic porous anion exchanger and the monolithic organic porous cation exchanger. Therefore, the error is reduced compared to the case in which only the monolithic organic porous anion exchanger is used to carry out the impurity capturing step, thereby analyzing the content of the metal impurities that are easily captured by the monolithic organic porous anion exchanger, and only the monolithic organic porous cation exchanger is used to carry out the impurity capturing step, thereby analyzing the content of the metal impurities that are easily captured by the monolithic organic porous cation exchanger, that is, the case in which cationic elements and anionic elements are separately analyzed by using different waters to be analyzed and different eluents and the content of all metal impurities in the waters to be analyzed is determined from these results. In particular, when the metal impurity content in the water to be analyzed is very low, for example, 1 ppt or less, the passing amount of the water to be analyzed into the adsorbent needs to be very high, and therefore the method for analyzing the metal impurity elements in the third embodiment of the present invention has a noticeable effect of reducing the error.

A kit for analyzing the metal impurity content of the first embodiment of the present invention (analytical apparatus) is a kit for analyzing the metal impurity content (analytical apparatus) that is characterized by comprising:
  a flow cell (1) that comprises at least a monolithic organic porous anion exchanger for passing water to be analyzed through the monolithic organic porous cation exchanger; and
  an integrating flowmeter for calculating an amount of water to be analyzed that has passed through the flow cell.

The kit for analyzing the metal impurity content of the first embodiment of the present invention is an analytical kit for performing the method for analyzing the metal impurity content of the first embodiment of the present invention.

The monolithic organic porous anion exchanger and the water to be analyzed according to the kit for analyzing the metal impurity content of the first embodiment of the present invention are the same as the monolithic organic porous anion exchanger and the water to be analyzed according to the method for analyzing the metal impurity content of the first embodiment of the present invention.

A kit for analyzing the metal impurity content of the second embodiment of the present invention (analytical apparatus) is a kit for analyzing the metal impurity content (analytical apparatus) that is characterized by comprising:

a flow cell (2) that comprises at least a monolithic organic porous cation exchanger for passing water to be analyzed through the monolithic organic porous cation exchanger; and an integrating flowmeter for calculating an amount of water to be analyzed that has passed through the flow cell.

The kit for analyzing the metal impurity content of the second embodiment of the present invention is an analytical kit for performing the method for analyzing the metal impurity content of the second embodiment of the present invention.

The monolithic organic porous cation exchanger and the water to be analyzed according to the kit for analyzing the metal impurity content of the second embodiment of the present invention are the same as the monolithic organic porous cation exchanger and the water to be analyzed according to the method for analyzing the metal impurity content of the second embodiment of the present invention.

A kit for analyzing the metal impurity content of the third embodiment of the present invention (analytical apparatus) is a kit for analyzing the metal impurity content (analytical apparatus) that is characterized by comprising:

a flow cell (3) that comprises at least a monolithic organic porous cation exchanger in a foregoing stage and a monolithic organic porous anion exchanger in a subsequent stage for passing water to be analyzed firstly through the monolithic organic porous cation exchanger and then through the monolithic organic porous anion exchanger, or that comprises a monolithic organic porous anion exchanger in a foregoing stage and a monolithic organic porous cation exchanger in a subsequent stage for passing water to be analyzed firstly through the monolithic organic porous anion exchanger and then through the monolithic organic porous cation exchanger; and an integrating flowmeter for calculating an amount of water to be analyzed that has passed through the flow cell.

The kit for analyzing the metal impurity content of the third embodiment of the present invention is an analytical kit for performing the method for analyzing the metal impurity content of the third embodiment of the present invention.

The monolithic organic porous cation exchanger, the monolithic organic porous anion exchanger, and the water to be analyzed according to the kit for analyzing the metal impurity content of the third embodiment of the present invention are the same as the monolithic organic porous cation exchanger, the monolithic organic porous anion exchanger, and the water to be analyzed according to the method for analyzing the metal impurity content of the third embodiment of the present invention.

The flow cells ((1), (2), and (3)) according to the kit for analyzing the metal impurity content of the first embodiment of the present invention, the kit for analyzing the metal impurity content of the second embodiment of the present invention, and the kit for analyzing the metal impurity content of the third embodiment of the present invention (hereinafter, the kit for analyzing the metal impurity content of the first embodiment of the present invention, the kit for analyzing the metal impurity content of the second embodiment of the present invention, and the kit for analyzing the metal impurity content of the third embodiment of the present invention are collectively referred to as the kit for analyzing the metal impurity content of the present invention) are the same except that the type of monolithic organic porous ion exchanger provided inside is different.

There is no particular limitation on the integrating flowmeter according to the kit for analyzing the metal impurity content of the present invention as long as it is capable of measuring and integrating the amount of liquid introduced.

The kit for analyzing the metal impurity content of the present invention has: a supply pipe for supplying the water to be analyzed and the eluent to the monolithic organic porous ion exchanger in the flow cell ((1), (2), or (3)); an introduction pipe for introducing the effluent discharged from the monolithic organic porous ion exchanger into the integrating flowmeter; and a discharge pipe for discharging the effluent discharged from the integrating flowmeter to the outside of the analytical kit.

The kit for analyzing the metal impurity content of the present invention is provided with a sealing means for sealing the inside of the kit to prevent contamination to the inside after removing the analytical kit from the pipe to which the water to be analyzed is supplied.

As the monolithic organic porous cation exchanger according to the kit for analyzing the metal impurity content of the present invention, preferable is the second monolithic cation exchanger, that is, a monolithic organic porous cation exchanger that is a co-continuous structural material formed of a three dimensionally continuous framework comprising an aromatic vinyl polymer containing 0.1 to 5.0 mol % of crosslinked structural units among the entire constituent units, with an average thickness of 1 to 60 µm in a dry state, and three dimensionally continuous pores in the framework with an average diameter of 10 to 200 µm in a dry state; has a total pore volume of 0.5 to 10 mL/g in a dry state; has cation exchange groups; has a cation exchange capacity per volume in a water wet state of 0.3 to 5.0 mg equivalent/mL (water wet state); and has the cation exchange groups uniformly distributed in the organic porous cation exchanger and also being the H form in that the passing speed can be increased and the time required for the impurity capturing step and the elution step can be shortened.

As the monolithic organic porous anion exchanger according to the kit for analyzing the metal impurity content of the present invention, preferable is the second monolithic anion exchanger, that is, a monolithic organic porous anion exchanger that is a co-continuous structural material formed of a three dimensionally continuous framework comprising an aromatic vinyl polymer containing 0.1 to 5.0 mol % of crosslinked structural units among the entire constituent units, with an average thickness of 1 to 60 µm in a dry state, and three dimensionally continuous pores in the framework with an average diameter of 10 to 200 µm in a dry state; has a total pore volume of 0.5 to 10 mL/g in a dry state; has anion exchange groups; has an anion exchange capacity per volume in a water wet state of 0.2 to 5.0 mg equivalent/mL (water wet state); and has the anion exchange groups uniformly distributed in the organic porous anion exchanger and also being the OH form in that the passing speed can be increased and the time required for the impurity capturing step and the elution step can be shortened.

Next, Examples will be given to illustrate the present invention in detail, but these are merely examples and do not limit the present invention.

EXAMPLES

The second monolithic cation exchanger was produced by the same method as Reference Example 17 of Examples in the specification according to Japanese Patent Laid-Open No. 2010-234357.

Reference Example 1

<Production of Second Monolithic Anion Exchanger and Second Monolithic Cation Exchanger>
(Step I; Production of Monolithic Intermediate)

5.4 g of styrene, 0.17 g of divinylbenzene, 1.4 g of sorbitan monooleate (hereinafter, abbreviated as SMO), and 0.26 g of 2,2'-azobis(isobutyronitrile) were mixed and uniformly dissolved. Next, the styrene/divinylbenzene/SMO/2,2'-azobis(isobutyronitrile) mixture was added to 180 g of pure water and stirred under reduced pressure in the temperature range of 5 to 20° C. using Vacuum Mixing & Degassing Mixer (available from EME CORPORATION), which is a planetary stirring apparatus, to obtain a water in oil type emulsion. This emulsion was immediately transferred to a reaction vessel and allowed to be polymerized under static conditions at 60° C. for 24 hours after sealing. After the completion of polymerization, the contents were taken out, extracted with methanol, and then dried under reduced pressure to produce a monolithic intermediate having a continuous macropore structure. The internal structure of the monolithic intermediate (dried material) thus obtained was observed with SEM images, and it was found that the wall part dividing two adjacent macropores was very thin and rod-like, but had a continuous bubble structure, and the apertures (mesopores), which were the overlapping portions of macropores with each other, had an average diameter of 70 µm and a total pore volume of 21.0 ml/g, as measured by the mercury injection method.
(Production of Monolith with Co-Continuous Structure)

Then, 76.0 g of styrene, 4.0 g of divinylbenzene, 120 g of 1-decanol, and 0.8 g of 2,2'-azobis(2,4-dimethylvaleronitrile) were mixed and uniformly dissolved (step II). Next, by cutting the above monolithic intermediate into a disc with a diameter of 70 mm and a thickness of about 40 mm, 4.1 g was separated. The separated monolithic intermediate was placed in a reaction vessel with an inner diameter of 110 mm and immersed in the styrene/divinylbenzene/1-decanol/2,2'-azobisis (2,4-dimethylvaleronitrile) mixture. After defoaming in a reduced pressure chamber, the reaction vessel was sealed and the mixture was polymerized under static conditions at 60° ° C. for 24 hours. After the completion of polymerization, the monolithic content with a thickness of about 60 mm was taken out, soxhlet extracted with acetone, and then dried at 85° C. under reduced pressure overnight (step III).

The internal structure of the monolith (dried material) thus obtained, containing 3.2 mol % of crosslinked components formed of the styrene/divinylbenzene copolymer, was observed with SEM, and it was found that the monolith had a co-continuous structure in which the framework and pores were three dimensionally continuous and both phases were intertwined. In addition, the thickness of the framework measured from SEM images was 17 µm. Also, the size of the three dimensionally continuous pores in the monolith was 41 µm and the total pore volume was 2.9 ml/g, as measured by the mercury injection method.

(Production of Monolithic Anion Exchanger with Co-Continuous Structure)

The monolith produced by the method described above was cut into a disc with a diameter of 70 mm and a thickness of about 50 mm. To this, 4700 ml of dimethoxymethane and 67 ml of tin tetrachloride were added, and 1870 ml of chlorosulfuric acid was added dropwise under ice cooling. After the completion of dropwise addition, the temperature was raised and the reaction was allowed at 35° C. for 5 hours, introducing chloromethyl groups. After the completion of reaction, the mother liquor was drained out with a siphon, and the monolith was washed with a mixed solvent of THF/water=2/1 and further washed with THF. To this chloromethylated monolithic organic porous material, 3400 ml of THE and 2000 ml of a 30% aqueous solution of trimethylamine were added and the mixture was allowed to react at 60° C. for 6 hours. After the completion of reaction, the product was washed with a mixed solvent of methanol/water and then washed with pure water to isolate it. As such, a monolithic anion exchanger A having a co-continuous structure was obtained.
(Production of Monolithic Cation Exchanger with Co-Continuous Structure)

The monolith produced by the method described above was cut into a disc with a diameter of 75 mm and a thickness of about 15 mm. The weight of the monolith was 18 g. To this, 1500 ml of dichloromethane was added, the mixture was heated at 35° C. for 1 hour and then cooled to 10° C. or lower, 99 g of chlorosulfuric acid was gradually added, and the temperature was raised and the reaction was allowed at 35° C. for 24 hours. Subsequently, methanol was added and the remaining chlorosulfuric acid was quenched, the mixture was washed with methanol to remove dichloromethane, and further washed with pure water to obtain a monolithic cation exchanger B having a co-continuous structure.
(Analysis for Monolithic Anion Exchanger A)

The obtained monolithic anion exchanger A was partially cut out and dried, and then its internal structure was observed by SEM, and it was confirmed that the monolithic anion exchanger maintained its co-continuous structure. Also, the swelling rate of the monolithic anion exchanger A before and after the reaction was 1.4 times, and the anion exchange capacity per volume in a water wet state was 0.72 mg equivalent/ml. When the size of the continuous pores of the monolith in a water wet state was estimated based on the value of the monolith and the swelling rate of the cation exchanger in a water wet state, it was 70 µm, and the diameter of the framework was 23 µm and the total pore volume was 2.9 ml/g.

In addition, the differential pressure coefficient, which is an index of the pressure loss when water is allowed to permeate through, was 0.005 MPa/m·LV. Furthermore, the length of the ion exchange zone for chloride ions in the monolithic anion exchanger A was measured, and the length of the ion exchange zone at LV=20 m/h was 16 mm.

Next, in order to confirm the distribution state of quaternary ammonium groups in the monolithic anion exchanger A, the anion exchanger A was treated with an aqueous hydrochloric acid solution to make them into the chloride form, and then the distribution state of chlorine atoms was observed by EPMA. As a result, it was observed that the quaternary ammonium groups were uniformly introduced into the framework surface and inside the framework (in the cross sectional direction) of the anion exchanger.
(Analysis for Monolithic Cation Exchanger B)

Also, the obtained monolithic cation exchanger B was partially cut out and dried, and then its internal structure was observed by SEM, and it was confirmed that the monolithic cation exchanger maintained its co-continuous structure. In addition, the swelling rate of the monolithic cation exchanger B before and after the reaction was 1.4 times, and the cation exchange capacity per volume in a water wet state was 0.72 mg equivalent/ml. When the size of the continuous pores of the monolith in a water wet state was estimated based on the value of the monolith and the swelling rate of the cation exchanger in a water wet state, it was 70 μm, and the diameter of the framework was 23 μm and the total pore volume was 2.9 ml/g.

In addition, the differential pressure coefficient, which is an index of the pressure loss when water is allowed to permeate through, was 0.005 MPa/m·LV. Furthermore, the length of the ion exchange zone for sodium ions in the monolithic cation exchanger B was measured, and the length of the ion exchange zone at LV=20 m/h was 16 mm, which was not only overwhelmingly shorter than the value (320 mm) of a commercially available strong acidic cation exchange resin, Amberlite IR120B (available from Rohm and Haas Company), but also shorter than the values of conventional monolithic porous cation exchangers having a continuous bubble structure.

Next, in order to confirm the distribution state of sulfonic acid groups in the monolithic cation exchanger B, the distribution state of sulfur atoms was observed by EPMA. As a result, it was observed that the sulfonic acid groups were uniformly introduced into the framework surface and inside the framework (in the cross sectional direction) of the cation exchanger.

Example 1

The monolithic anion exchanger A was cut into a shape with a diameter of 10 mm and a height of 20 mm and filled into a filling container made of PFA (tetrafluoroethylene-perfluoroalkyl vinyl ether copolymer). Then, a test water 1, which will be mentioned later, was passed through the inside of the filling container at 33 mL/min. (SV=1274 h$^{-1}$) under the conditions shown in Table 1, and the test water 1 was passed through the monolithic anion exchanger A. The total passing amount of the test water 1 at this time is 100 mL.

Next, the collected liquid was measured by ICP-MS to measure the concentration of each ionic impurity element.

Then, the total amount of each ionic impurity element in the test water that had passed through and the total collection amount of each ionic impurity element in the collected liquid were determined by calculating from the concentration of each ionic impurity element in the test water and the total passing amount thereof, and by calculating from the concentration of each ionic impurity element in the collected liquid and the passing amount of the liquid, respectively. And, the percentage of the total collection amount of each ionic impurity element in the collected liquid relative to the total amount of each ionic impurity element in the test water that had passed through was determined. The results are shown in Table 2.

(Test Water 1)

A test water adjusted to contain each of Li, B, Na, Mg, Al, K, Ca, Ti, V, Cr, Mn, Fe, Co, Ni, Cu, Zn, Ga, As, Cd, Sn, Ba, and Pb at 2000 ng/L.

(Analysis)

The content of each element in the test water and the treated water was measured by ICP-MS (available from Agilent Technologies, Inc., 7500 cs).

Note that, in the analysis for the content by ICP-MS, a plurality of standard samples with different contents were used in advance to create a calibration curve for the count value (CPS) and the metal content, the test sample (test water or treated water) was measured, and a metal content corresponding to that count value was defined as the metal content of the test water or treated water, based on the calibration curve.

Example 2

The same procedure as in Example 1 was carried out except that the monolithic cation exchanger B was cut into the shape shown in Table 1 and the liquid was passed therethrough under the conditions shown in Table 1. The results are shown in Table 2.

Example 3

The same procedure as in Example 1 was carried out except that both the monolithic anion exchanger A and the monolithic cation exchanger B were cut into the shape shown in Table 1, the filling container was filled with the monolithic cation exchanger B in the foregoing stage and the monolithic anion exchanger A in the subsequent stage, and the liquid was passed therethrough under the conditions shown in Table 1. The results are shown in Table 2.

Example 4

The same procedure as in Example 1 was carried out except that both the monolithic anion exchanger A and the monolithic cation exchanger B were cut into the shape shown in Table 1, the filling container was filled with the monolithic anion exchanger A in the foregoing stage and the monolithic cation exchanger B in the subsequent stage, and the liquid was passed therethrough under the conditions shown in Table 1. The results are shown in Table 2.

Comparative Example 1

The same procedure as in Example 1 was carried out except that a particulate anion exchange resin (available from The Dow Chemical Company, AMBERJET ESG 4002 (OH), average particle diameter: 0.5 to 0.65 μm, ion exchange capacity in wet state: 1.25 mg equivalent/g, anion exchange group: quaternary ammonium) was filled into the filling container to form a filling layer with the shape shown in Table 1 and the liquid was passed therethrough under the conditions shown in Table 1. The results are shown in Table 2.

Comparative Example 2

The same procedure as in Example 1 was carried out except that a particulate cation exchange resin (available from The Dow Chemical Company, model number: AMBERJET 1024 (H), average particle diameter: 0.60 to 0.70 mm, ion exchange capacity in wet state: 2.1 mg equivalent/g or more, cation exchange group: sulfonic acid group) was filled into the filling container to form a filling layer with the shape shown in Table 1 and the liquid was passed therethrough under the conditions shown in Table 1. The results are shown in Table 2.

Comparative Example 3

The same procedure as in Example 1 was carried out except that the particulate anion exchange resin used in Comparative Example 2 and the particulate cation exchange resin used in Comparative Example 3 were mixed in a volume ratio of 1:1, the mixture was filled into the filling container to form a filling layer with the shape shown in Table 1, and the liquid was passed therethrough under the conditions shown in Table 1. The results are shown in Table 2.

Comparative Example 4

A membrane module was fabricated by the method described in T. Hori et al., J. Membr. Sci., 132 (1997) 203-211 (ion exchange groups per g of membrane: 1.6 mg equivalent, average pore diameter: 0.1 µm, exchange group: sulfonic acid group). Then, the test water was supplied into the membrane module at 76 mL/min. (SV=1274 h$^{-1}$), and the test water was passed through the cation adsorption membrane. The total passing amount of the test water at this time is 100 mL.

Next, the collected liquid was measured by ICP-MS to measure the concentration of each ionic impurity element.

Then, in the same manner as in Example 1, the percentage of the total collection amount of each ionic impurity element in the collected liquid relative to the total amount of each ionic impurity element in the test water that had passed through was determined. The results are shown in Table 2.

The monolithic organic porous anion exchanger of Example 1 has excellent adsorption performance for B and As, for which the monolithic organic porous cation exchanger has insufficient adsorption performance. Excellent adsorption performance was exhibited for Al, V, Ti, Cr, Fe, Cu, Zn, Ga, Sn, and Pb as well.

The monolithic organic porous cation exchanger of Example 2 exhibited excellent adsorption performance except for B, As and Cd.

In Examples 3 and 4, by combining the monolithic organic porous cation exchanger and the monolithic organic porous anion exchanger, all of the elements described above could be completely adsorbed. Especially for Cd, neither the monolithic organic porous cation exchanger nor the monolithic organic porous anion exchanger has sufficient adsorption performance by itself, whereas the combination of the monolithic organic porous cation exchanger and the monolithic organic porous anion exchanger could completely adsorb Cd.

On the other hand, all of Comparative Examples 1 to 3, which use ion exchange resins have adsorption performance significantly inferior to that of the monolithic organic porous cation exchanger or the monolithic organic porous anion exchanger.

TABLE 1

|  |  | Example 1 | Example 2 | Example 3 | Example 4 | Comparative Example 1 | Comparative Example 2 | Comparative Example 3 | Comparative Example 4 |
|---|---|---|---|---|---|---|---|---|---|
|  |  | Monolith | | | | Ion exchange resin | | | Ion exchange membrane |
| Ion exchanger Type | | Anion | Cation | Cation foregoing stage Anion subsequent stage | Anion foregoing stage Cation subsequent stage | Anion | Cation | Anion + Cation | Cation |
| Ø | mm | 10 | 10 | 10 | 10 | 10 | 10 | 10 | 15.6 |
| Layer height | mm | 20 | 20 | 40 | 40 | 20 | 20 | 40 | 20 |
| Volume | ml | 1.6 | 1.6 | 3.1 | 3.1 | 1.6 | 1.6 | 3.1 | 3.8 |
| Water passing flow rate | L/h | 2 | 2 | 2 | 2 | 2 | 2 | 2 | 4.9 |
| Passing amount | ml | 100 | 100 | 100 | 100 | 100 | 100 | 100 | 100 |
| SV | h$^{-1}$ | 1274 | 1274 | 637 | 637 | 1274 | 1274 | 637 | 1273 |
| LV | m/h | 25 | 25 | 25 | 25 | 25 | 25 | 25 | 25 |

TABLE 2

|  | Li | B | Na | Mg | Al | K | Ca | Ti | V | Cr | Mn | Fe | Co |
|---|---|---|---|---|---|---|---|---|---|---|---|---|---|
| Example 1 | 29% | >99% | 10% | 16% | >99% | 21% | 6% | >99% | >99% | >99% | 15% | >99% | 19% |
| Example 2 | >99% | 29% | >99% | >99% | >99% | >99% | >99% | >99% | >99% | >99% | >99% | >99% | >99% |
| Example 3 | >99% | >99% | >99% | >99% | >99% | >99% | >99% | >99% | >99% | >99% | >99% | >99% | >99% |
| Example 4 | >99% | >99% | >99% | >99% | >99% | >99% | >99% | >99% | >99% | >99% | >99% | >99% | >99% |
| Comparative Example 1 | 12% | 81% | 10% | 14% | 33% | 13% | 10% | 44% | 63% | 19% | 15% | 32% | 15% |
| Comparative Example 2 | 68% | 0% | 68% | 68% | 63% | 48% | 44% | 63% | 68% | 65% | 71% | | |
| Comparative Example 3 | 53% | 80% | 36% | 25% | 31% | 30% | 22% | 40% | 60% | 20% | 17% | 16% | 32% |
| Comparative Example 4 | >99% | 10% | >99% | >99% | >99% | >99% | >99% | >99% | >99% | >99% | >99% | >99% | >99% |

|  | Ni | Cu | Zn | Ga | As | Cd | Sn | Ba | Pb |
|---|---|---|---|---|---|---|---|---|---|
| Example 1 | 24% | >99% | >99% | >99% | >99% | 34% | >99% | 18% | >99% |
| Example 2 | >99% | >99% | >99% | >99% | 10% | 91% | >99% | >99% | >99% |
| Example 3 | >99% | >99% | >99% | >99% | >99% | >99% | >99% | >99% | >99% |
| Example 4 | >99% | >99% | >99% | >99% | >99% | >99% | >99% | >99% | >99% |
| Comparative Example 1 | 2% | 18% | 18% | 50% | 80% | 17% | 65% | 4% | 7% |
| Comparative Example 2 | 51% | 71% | 47% | 61% | 0% | 39% | 50% | 58% | 71% |
| Comparative Example 3 | 32% | 35% | 43% | 33% | 63% | 30% | 64% | 50% | 25% |
| Comparative Example 4 | >99% | >99% | >99% | >99% | 12% | 80% | >99% | >99% | >99% |

Also, when the cation exchange membrane of Comparative Example 4 was used, it exhibited excellent adsorption performance except for B, As and Cd, which was comparable to that of the monolithic organic porous cation exchanger.

Next, the monolithic organic porous anion exchanger, the monolithic organic porous cation exchanger, and the cation exchange membrane, all of which had high adsorption performance in the above test, were subjected to a collection performance test with an eluent. Note that the collection performance test was not carried out for the anion exchange resin and the cation exchange resin because of their inferior adsorption performance.

Example 5

The monolithic anion exchanger A was cut into a shape with a diameter of 10 mm and a height of 20 mm and filled into a filling container made of PFA (tetrafluoroethylene-perfluoroalkyl vinyl ether copolymer). Then, the test water was passed through the inside of the filling container at 33 mL/min. (SV=1274 h$^{-1}$) under the conditions shown in Table 3, and the test water 1 was passed through the monolithic anion exchanger A. The total passing amount of the test water 1 at this time is 100 mL.

Next, 200 mL of an aqueous 1 N nitric acid solution (TAMAPURE-AA-10 available from Tama Chemicals Co., Ltd., the content of each metal element in Table 2 and Table 4 is 10 ppt or less) was passed through the monolithic anion exchanger A as the eluent, and the collected eluent was obtained. Note that, for the passing of the aqueous 1 N nitric acid solution, 200 mL was passed through as the total passing amount, and for 0 to 100 mL, 20 mL was separately taken each time, and for 100 to 200 mL, 100 mL was collected.

Next, the collected eluent was measured by ICP-MS to measure the concentration of each ionic impurity element.

Then, the total amount of each ionic impurity element in the test water that had passed through and the total elution and collection amount of each ionic impurity element in the collected eluent were determined by calculating from the concentration of each ionic impurity element in the test water and the total passing amount thereof, and by calculating from the concentration of each ionic impurity element in the collected eluent and the passing amount of the eluent, respectively. And, the percentage of the total elution and collection amount of each ionic impurity element in the collected eluent relative to the total amount of each ionic impurity element in the test water that had passed through was determined. The results are shown in Table 4. For the collection amount column in Table 2, "20 ml" in the collection column refers to the "collected liquid with an integrated amount of collected liquid of 0 to 20 ml", "40 ml" in the collection column refers to the "collected liquid with an integrated amount of collected liquid of 0 to 40 ml", "60 ml" in the collection column refers to the "collected liquid with an integrated amount of collected liquid of 0 to 60 ml", "80 ml" in the collection column refers to the "collected liquid with an integrated amount of collected liquid of 0 to 80 ml", "100 ml" in the collection column refers to the "collected liquid with an integrated amount of collected liquid of 0 to 100 ml", and "200 ml" in the collection column refers to the "collected liquid with an integrated amount of collected liquid of 0 to 200 ml". The same applies to Table 5 to Table 8 below.

TABLE 3

| Ion exchanger Type | | Example 5 Monolith Anion | Example 6 Monolith Cation | Example 7 Monolith Cation foregoing stage Anion subsequent stage | Example 8 Monolith Anion foregoing stage Cation subsequent stage | Comparative Example 5 Ion exchange resin Cation |
|---|---|---|---|---|---|---|
| Water passing conditions of test water | | | | | | |
| Ø | mm | 10 | 10 | 10 | 10 | 15.6 |
| Layer height | mm | 20 | 20 | 40 | 40 | 20 |
| Volume | ml | 1.6 | 1.6 | 3.1 | 3.1 | 3.8 |
| Water passing flow rate | L/h | 2 | 2 | 2 | 2 | 4.9 |
| Passing amount | ml | 100 | 100 | 100 | 100 | 100 |
| SV | h$^{-1}$ | 1274 | 1274 | 637 | 637 | 1273 |
| LV | m/h | 25 | 25 | 25 | 25 | 25 |
| Passing conditions of eluent | | | | | | |
| Water passing flow rate | L/h | 1.5 | 1.5 | 1.5 | 1.5 | 1.5 |
| Passing amount | ml | 200 | 200 | 200 | 200 | 200 |
| SV | h$^{-1}$ | 955 | 955 | 478 | 478 | 393 |
| LV | m/h | 19 | 19 | 19 | 19 | 8 |

TABLE 4

| Collection amount [ml] | Li | B | Na | Mg | Al | K | Ca | Ti | V | Cr | Mn | Fe | Co |
|---|---|---|---|---|---|---|---|---|---|---|---|---|---|
| 20 | 0% | 100% | 9% | 16% | 76% | 1% | 15% | 89% | 88% | 95% | 1% | 82% | 3% |
| 40 | 0% | 105% | 9% | 18% | 88% | 1% | 16% | 98% | 96% | 98% | 1% | 95% | 3% |
| 60 | 0% | 105% | 9% | 19% | 93% | 1% | 16% | 101% | 98% | 98% | 1% | 103% | 3% |

TABLE 4-continued

| | | | | | | | | | | | | | |
|---|---|---|---|---|---|---|---|---|---|---|---|---|---|
| 80 | 0% | 105% | 9% | 20% | 96% | 1% | 16% | 103% | 100% | 98% | 2% | 105% | 4% |
| 100 | 0% | 105% | 9% | 20% | 97% | 1% | 16% | 103% | 100% | 98% | 2% | 105% | 4% |
| 200 | 0% | 105% | 9% | 21% | 98% | 1% | 17% | 104% | 101% | 98% | 2% | 105% | 4% |

| Collection amount [ml] | Ni | Cu | Zn | Ga | As | Cd | Sn | Ba | Pb |
|---|---|---|---|---|---|---|---|---|---|
| 20 | 10% | 98% | 90% | 81% | 87% | 18% | >120% | 3% | 24% |
| 40 | 10% | 100% | 94% | 94% | 94% | 20% | >120% | 3% | 27% |
| 60 | 10% | 103% | 96% | 99% | 96% | 21% | >120% | 3% | 28% |
| 80 | 10% | 103% | 96% | 101% | 97% | 21% | >120% | 3% | 28% |
| 100 | 10% | 103% | 96% | 102% | 98% | 21% | >120% | 3% | 28% |
| 200 | 10% | 103% | 96% | 103% | 99% | 21% | >120% | 4% | 28% |

Example 6

The same procedure as in Example 5 was carried out except that the monolithic cation exchanger B was cut into the shape shown in Table 3 and the liquid was passed therethrough under the conditions shown in Table 3. The results are shown in Table 5.

TABLE 5

| Collection amount [ml] | Li | B | Na | Mg | Al | K | Ca | Ti | V | Cr | Mn | Fe | Co |
|---|---|---|---|---|---|---|---|---|---|---|---|---|---|
| 20 | 96% | 0% | 101% | 83% | 80% | 86% | 90% | 90% | 41% | 11% | 82% | 13% | 80% |
| 40 | 96% | 0% | 102% | 91% | 89% | 88% | 103% | 94% | 63% | 60% | 93% | 66% | 90% |
| 60 | 97% | 0% | 102% | 91% | 93% | 88% | 104% | 94% | 71% | 86% | 94% | 96% | 90% |
| 80 | 97% | 0% | 103% | 91% | 94% | 88% | 105% | 94% | 73% | 91% | 94% | 102% | 90% |
| 100 | 97% | 0% | 103% | 92% | 94% | 88% | 105% | 94% | 74% | 93% | 94% | 104% | 90% |
| 200 | 97% | 0% | 103% | 92% | 95% | 88% | 106% | 94% | 74% | 94% | 95% | 106% | 91% |

| Collection amount [ml] | Ni | Cu | Zn | Ga | As | Cd | Sn | Ba | Pb |
|---|---|---|---|---|---|---|---|---|---|
| 20 | 89% | 97% | 78% | 9% | 4% | 87% | 59% | 66% | 99% |
| 40 | 91% | 106% | 85% | 63% | 4% | 91% | 88% | 88% | 100% |
| 60 | 92% | 106% | 85% | 91% | 4% | 92% | 90% | 90% | 101% |
| 80 | 92% | 106% | 86% | 97% | 4% | 92% | 90% | 90% | 101% |
| 100 | 92% | 106% | 86% | 98% | 4% | 92% | 90% | 90% | 101% |
| 200 | 92% | 107% | 86% | 99% | 4% | 92% | 91% | 90% | 101% |

Example 7

The same procedure as in Example 1 was carried out except that both the monolithic anion exchanger A and the monolithic cation exchanger B were cut into the shape shown in Table 3, the filling container was filled with the monolithic cation exchanger B in the foregoing stage and the monolithic anion exchanger A in the subsequent stage, and the liquid was passed therethrough under the conditions shown in Table 3. The results are shown in Table 6.

TABLE 6

| Collection amount [ml] | Li | B | Na | Mg | Al | K | Ca | Ti | V | Cr | Mn | Fe | Co |
|---|---|---|---|---|---|---|---|---|---|---|---|---|---|
| 20 | 65% | 74% | 101% | 84% | 68% | 71% | 90% | 69% | 56% | 95% | 68% | 13% | 68% |
| 40 | 74% | 74% | 102% | 105% | 88% | 82% | 103% | 82% | 73% | 98% | 86% | 66% | 87% |
| 60 | 77% | 75% | 102% | 108% | 92% | 85% | 104% | 84% | 76% | 98% | 89% | 96% | 89% |
| 80 | 78% | 75% | 103% | 110% | 93% | 86% | 105% | 86% | 77% | 98% | 90% | 102% | 90% |
| 100 | 79% | 75% | 103% | 111% | 94% | 86% | 105% | 86% | 78% | 98% | 90% | 104% | 91% |
| 200 | 79% | 75% | 103% | 111% | 95% | 87% | 106% | 87% | 78% | 98% | 91% | 106% | 91% |

| Collection amount [ml] | Ni | Cu | Zn | Ga | As | Cd | Sn | Ba | Pb |
|---|---|---|---|---|---|---|---|---|---|
| 20 | 89% | 81% | 62% | 32% | 88% | 62% | >120% | 59% | 81% |
| 40 | 91% | 100% | 76% | 99% | 91% | 77% | >120% | 82% | 104% |
| 60 | 92% | 103% | 78% | 107% | 92% | 80% | >120% | 85% | 107% |
| 80 | 92% | 104% | 80% | 108% | 92% | 81% | >120% | 86% | 109% |
| 100 | 92% | 105% | 80% | 109% | 92% | 82% | >120% | 86% | 109% |
| 200 | 92% | 105% | 81% | 109% | 93% | 82% | >120% | 87% | 110% |

Example 8

The same procedure as in Example 1 was carried out except that both the monolithic anion exchanger A and the monolithic cation exchanger B were cut into the shape shown in Table 3, the filling container was filled with the monolithic anion exchanger A in the foregoing stage and the monolithic cation exchanger B in the subsequent stage, and the liquid was passed therethrough under the conditions shown in Table 3. The results are shown in Table 7.

TABLE 7

| Collection amount [ml] | Li | B | Na | Mg | Al | K | Ca | Ti | V | Cr | Mn | Fe | Co |
|---|---|---|---|---|---|---|---|---|---|---|---|---|---|
| 20 | 73% | 77% | 101% | 70% | 26% | 75% | 67% | 69% | 65% | 95% | 67% | 13% | 62% |
| 40 | 79% | 80% | 102% | 93% | 68% | 84% | 102% | 82% | 75% | 98% | 89% | 66% | 83% |
| 60 | 80% | 82% | 102% | 95% | 80% | 84% | 104% | 86% | 78% | 98% | 91% | 96% | 85% |
| 80 | 80% | 83% | 103% | 95% | 85% | 85% | 105% | 88% | 79% | 98% | 91% | 102% | 85% |
| 100 | 80% | 84% | 103% | 96% | 89% | 85% | 105% | 90% | 80% | 98% | 91% | 104% | 85% |
| 200 | 80% | 84% | 103% | 96% | 91% | 85% | 105% | 90% | 81% | 98% | 91% | 106% | 85% |

| Collection amount [ml] | Ni | Cu | Zn | Ga | As | Cd | Sn | Ba | Pb |
|---|---|---|---|---|---|---|---|---|---|
| 20 | 89% | 62% | 59% | 14% | 77% | 68% | >120% | 55% | 71% |
| 40 | 91% | 88% | 78% | 65% | 85% | 86% | >120% | 88% | 94% |
| 60 | 92% | 94% | 81% | 81% | 88% | 88% | >120% | 90% | 100% |
| 80 | 92% | 96% | 83% | 87% | 89% | 88% | >120% | 90% | 103% |
| 100 | 92% | 98% | 84% | 91% | 90% | 89% | >120% | 90% | 105% |
| 200 | 92% | 100% | 85% | 94% | 91% | 89% | >120% | 90% | 106% |

Comparative Example 5

The membrane module used in Comparative Example 4 was fabricated. Then, the test water was supplied into the membrane module under the conditions shown in Table 3, and the test water was passed through the cation adsorption membrane.

Next, 200 mL of the aqueous 1 N nitric acid solution was passed through the cation adsorption membrane as the eluent, and the collected eluent was obtained. Note that, for the passing of the aqueous 1 N nitric acid solution, 200 mL was passed through as the total passing amount, and for 0 to 100 mL, 20 mL was separately taken each time, and for 100 to 200 mL, 100 mL was collected.

Next, the collected eluent was measured by ICP-MS to measure the concentration of each ionic impurity element.

Then, the total amount of each ionic impurity element in the test water that had passed through and the total elution and collection amount of each ionic impurity element in the collected eluent were determined by calculating from the concentration of each ionic impurity element in the test water and the total passing amount thereof, and by calculating from the concentration of each ionic impurity element in the collected eluent and the passing amount of the eluent, respectively. And, the percentage of the total elution and collection amount of each ionic impurity element in the collected eluent relative to the total amount of each ionic impurity element in the test water that had passed through was determined. The results are shown in Table 8.

TABLE 8

| Collection amount [ml] | Li | B | Na | Mg | Al | K | Ca | Ti | V | Cr | Mn | Fe | Co |
|---|---|---|---|---|---|---|---|---|---|---|---|---|---|
| 20 | 96% | 0% | >120% | 50% | 28% | 86% | 39% | 42% | 41% | 13% | 22% | 4% | 45% |
| 40 | 98% | 0% | >120% | 104% | 42% | 98% | >120% | 64% | 63% | 25% | 66% | 16% | 98% |
| 60 | 99% | 0% | >120% | 107% | 56% | 99% | >120% | 64% | 71% | 38% | 76% | 33% | 106% |
| 80 | 99% | 0% | >120% | 107% | 73% | 99% | >120% | 64% | 73% | 56% | 77% | 52% | 106% |
| 100 | 99% | 0% | >120% | 107% | 82% | 99% | >120% | 64% | 74% | 67% | 77% | 68% | 106% |
| 200 | 99% | 0% | >120% | 107% | 82% | 99% | >120% | 64% | 74% | 67% | 77% | 68% | 106% |

| Collection amount [ml] | Ni | Cu | Zn | Ga | As | Cd | Sn | Ba | Pb |
|---|---|---|---|---|---|---|---|---|---|
| 20 | 29% | 57% | 61% | 32% | 7% | 32% | 11% | 2% | 19% |
| 40 | 74% | 111% | >120% | 64% | 7% | 91% | 50% | 12% | 82% |
| 60 | 80% | 117% | >120% | 82% | 7% | 98% | 73% | 26% | 110% |
| 80 | 81% | 117% | >120% | 82% | 7% | 98% | 84% | 40% | >120% |
| 100 | 81% | 117% | >120% | 82% | 7% | 98% | 91% | 53% | >120% |
| 200 | 81% | 117% | >120% | 83% | 7% | 98% | 91% | 53% | >120% |

The monolithic organic porous anion exchanger of Example 5 exhibited excellent collection performance for B and As, for which the monolithic organic porous cation exchanger has insufficient adsorption performance. Excellent collection performance was exhibited for V, Cr, and Fe as well.

The monolithic organic porous cation exchanger of Example 6 exhibited excellent adsorption performance except for B and As.

In Examples 7 and 8, by combining the monolithic organic porous cation exchanger and the monolithic organic porous anion exchanger, all of the elements described above could be completely collected.

Also, when the cation exchange membrane of Comparative Example 5 was used, it exhibited excellent collection performance except for B, Ti, V, Cr, Mn, Fe, As, and Ba.

Subsequently, for Example 5, Example 6, Example 7, Example 8, and Comparative Example 5, a test water 2, which will be mentioned later, was passed through under the water passing conditions shown in Table 3, and the test water 2 was passed through the ion exchanger. The total passing amount of the test water 2 at this time is 100 mL. Then, the total amount of metal impurity fine particles in the test water that had passed through and the total collection amount of metal impurity fine particles in the collected liquid were determined by calculating from the concentration of metal impurity fine particles in the test water and the total passing amount thereof, and by calculating from the concentration of metal impurity fine particles in the collected liquid and the passing amount of the liquid, respectively. And, the percentage of the total collection amount of metal impurity fine particles in the collected liquid relative to the total amount of metal impurity fine particles in the test water that had passed through was determined. The results are shown in Table 9.

(Test Water 2)

As the test water 2, a test water was prepared that was adjusted to have a content of 1000 ng/L for $Fe_3O_4$ fine particles with an average particle diameter of 5 nm (particle diameter: not less than 4 nm and less than 6 nm), $Fe_3O_4$ fine particles with an average particle diameter of 10 nm (particle diameter: not less than 9 nm and less than 11 nm), and $Fe_3O_4$ fine particles with an average particle diameter of 30 nm (particle diameter: not less than 29 nm and less than 31 nm). Note that the $Fe_3O_4$ fine particles in the test water 2 was prepared from an "iron oxide solution" available from Sigma-Aldrich Co. LLC. Note that the particle diameter was measured with a transmission electron microscope (TEM).

(Analysis)

The concentration of each fine particle in the test water and the collected eluent was determined by ICP-MS measurement.

Note that, in the analysis for the content by ICP-MS, a plurality of standard samples with different contents were used in advance to create a calibration curve for the count value (CPS) and the metal particle content, the test sample (test water or treated water) was measured, and a metal particle content corresponding to that count value was defined as the metal particle content of the test water or treated water, based on the calibration curve.

TABLE 9

|  | Fe 5 nm | Fe 10 nm | Fe 30 nm |
|---|---|---|---|
| Example 5 | 95% | 97% | >99% |
| Example 6 | 85% | 95% | 97% |

TABLE 9-continued

|  | Fe 5 nm | Fe 10 nm | Fe 30 nm |
|---|---|---|---|
| Example 7 | >99% | >99% | >99% |
| Example 8 | >99% | >99% | >99% |
| Comparative Example 5 | 85% | 95% | 97% |

* In Table 9, Fe 5 nm: $Fe_3O_4$ fine particles with an average particle diameter of 5 nm, Fe 10 nm: $Fe_3O_4$ fine particles with an average particle diameter of 10 nm, and Fe 30 nm: $Fe_3O_4$ fine particles with an average particle diameter of 30 nm.

The monolithic organic porous anion exchanger of Example 5 exhibited excellent adsorption performance for Fe particles with an average particle diameter of 5 nm and an average particle diameter of 10 nm, for which the monolithic organic porous cation exchanger has insufficient adsorption performance.

In Examples 7 and 8, by combining the monolithic organic porous cation exchanger and the monolithic organic porous anion exchanger, the Fe particles with different particle diameters could be completely adsorbed.

Also, when the cation exchange membrane of Comparative Example 5 was used, it exhibited adsorption performance comparable to that of the monolithic organic porous cation exchanger.

Next, 200 mL of the aqueous 1 N nitric acid solution was supplied into the filling container as the eluent and the aqueous 1 N nitric acid solution was passed through the ion exchanger, thereby obtaining the collected eluent.

Then, the collected eluent was measured (by ICP-MS) to measure the content of each fine particle. Note that the metal impurity fine particles adsorbed onto the monolithic organic porous ion exchanger exist in an ionic state in the collected eluent due to elution with an acid such as nitric acid. Also, in ICP-MS, ionization is carried out at high temperature. Therefore, even solid matter, such as metal impurity fine particles, can be ionized for analysis.

Then, the total amount of each fine particle in the test water 2 that had passed through and the total elution and collection amount of each fine particle in the collected eluent were determined by calculating from the content of each fine particle in the test water 2 and the total passing amount thereof, and by calculating from the content of each fine particle in the collected eluent and the passing amount of the eluent, respectively. And, the percentage of the total elution and collection amount of each fine particle in the collected eluent relative to the total amount of each fine particle in the test water 2 that had passed through was determined. The results are shown in Table 10.

TABLE 10

|  | Fe 5 nm | Fe 10 nm | Fe 30 nm |
|---|---|---|---|
| Example 5 | 85% | 90% | >99% |
| Example 6 | 20% | 45% | 50% |
| Example 7 | >99% | >99% | >99% |
| Example 8 | >99% | >99% | >99% |
| Comparative Example 5 | 20% | 40% | 50% |

* In Table 10, Fe 5 nm: $Fe_3O_4$ fine particles with an average particle diameter of 5 nm, Fe 10 nm: $Fe_3O_4$ fine particles with an average particle diameter of 10 nm, and Fe 30 nm: $Fe_3O_4$ fine particles with an average particle diameter of 30 nm.

The monolithic organic porous anion exchanger of Example 5 exhibited excellent collection performance for Fe particles with each particle diameter, for which the monolithic organic porous cation exchanger has insufficient adsorption performance.

In Examples 7 and 8, by combining the monolithic organic porous cation exchanger and the monolithic organic porous anion exchanger, the Fe particles with each particle diameter could be completely collected.

Also, the monolithic organic porous cation exchanger of Example 6 and the cation exchange membrane of Comparative Example 5 exhibited similar collection performance.

Example 9

The monolithic cation exchanger B was cut into a shape with a diameter of 10 mm and a height of 20 mm and filled into a filling container made of PFA (tetrafluoroethylene-perfluoroalkyl vinyl ether copolymer). Then, a test water 3, which will be mentioned later, was passed through the inside of the filling container under the conditions shown in Table 11, and the test water 3 was passed through the monolithic cation exchanger B.

Next, the aqueous 1 N nitric acid solution was supplied into the filling container as the eluent at the amount shown in Table 11 and the aqueous 1 N nitric acid solution was passed through the ion exchanger, thereby obtaining the collected eluent.

Then, the collected eluent was measured (by ICP-MS) to measure the content of each ionic impurity element.

Next, the content of each ionic impurity element in the test water 3 was determined from the total passing amount of the test water 3, the content of each ionic impurity element in the collected eluent, and the passing amount of the eluent. The results are shown in Table 12.

Note that the blank value in the present Example is less than 10 ng/L. In the present Example, the blank value refers to the higher numerical value among the lower limit of quantification of ICP-MS or the amount of metal elution from the monolith. For example, in the case where the blank value is less than 10 ng/L, whereas the lower limit of quantification required for the test water is 0.001 ng/L, a concentration factor of 10000 times is required, and therefore, a water passing amount that is 10000 times the water passing amount of the eluent is required.

(Test Water 3)

Ultrapure water sampled from an ultrapure water production facility was prepared as the test water 3.

Comparative Example 6

A membrane module was fabricated by the same method as in Comparative Example 4 (ion exchange groups per g of membrane: 1.6 mg equivalent, average pore diameter: 0.1 μm, exchange group: sulfonic acid group). Then, the test water 3, which will be mentioned later, was passed through the membrane module under the conditions shown in Table 11, thereby carrying out the passing of the test water 3 through the membrane module.

Thereafter, the same procedure was carried out as in Example 9. And, the content of each ionic impurity element in the test water 3 was determined from the total passing amount of the test water 3, the content of each ionic impurity element in the collected eluent, and the passing amount of the eluent. The results are shown in Table 12.

TABLE 11

| Ion exchanger Type | | Example 9 Monolith Cation | Comparative Example 6 Ion exchange membrane Cation |
|---|---|---|---|
| Supply pressure | MPa | | 0.1 |
| Pressure coefficient | L/min/MPa | 8.7 | 2 |
| Water passing flow rate | ml/min | 870 | 200 |
| Water passing amount | L | 1000 | 2000 |
| Water passing time | h | 19 | 167 |
| Blank value | ng/L | <10 | |
| Lower limit of quantification required | ng/L | 0.001 | |
| Concentration factor | — | 10000 | |
| Water passing amount of eluent | ml | 100 | 200 |
| Water passing amount required | L | 1000 | 2000 |

TABLE 12

| | Li | Na | Mg | Al | K | Ca | Ti | Cr | Mn | Fe | Co |
|---|---|---|---|---|---|---|---|---|---|---|---|
| Example 9 | <0.001 | 0.026 | 0.002 | 0.001 | 0.002 | 0.002 | <0.001 | 0.001 | 0.002 | 0.003 | <0.001 |
| Comparative Example 6 | <0.001 | 0.026 | 0.002 | 0.001 | 0.002 | 0.002 | <0.001 | 0.001 | 0.002 | 0.003 | <0.001 |

| | Ni | Cu | Zn | Cd | Sn | Ba | Pb |
|---|---|---|---|---|---|---|---|
| Example 9 | 0.016 | 0.001 | 0.001 | <0.001 | <0.001 | <0.001 | <0.001 |
| Comparative Example 6 | 0.016 | 0.001 | 0.001 | <0.001 | <0.001 | <0.001 | <0.001 |

Unit:ppt

From the results in Table 12, it was found that, in Example 9 using the monolithic cation exchanger B, the quantitative analysis for the metal impurity content in ultrapure water can be performed in the order of ppq with a similar accuracy as in Comparative Example 6 using the membrane module. In addition, it was found that Example 9 was able to complete the passing of the water to be analyzed in an amount required for the analysis in a very short water passing time compared to Comparative Example 6, thus significantly reducing the analysis time.

Example 10

The monolithic anion exchanger A was cut into a shape with a diameter of 10 mm and a height of 20 mm and filled into a filling container made of PFA (tetrafluoroethylene-perfluoroalkyl vinyl ether copolymer). Then, the test water 3, which will be mentioned later, was passed through the inside of the filling container under the conditions shown in Table 13, and the test water 3 was passed through the monolithic anion exchanger A.

Thereafter, the same procedure was carried out as in Example 9. And, the content of each ionic impurity element (B) in the test water 3 was determined from the total passing amount of the test water 3, the content of each ionic impurity element (B) in the collected eluent, and the passing amount of the eluent. As a result, the content of B in the collected eluent was 30 ppt. This value was greater than the lower limit of quantification of ICP-MS, which is 10 ppt. The content of B in the test water 3, calculated from the content of B in the collected eluent, is 0.3 ppt.

TABLE 13

| Ion exchanger Type | | Example 10 Monolith Anion |
|---|---|---|
| Supply pressure | MPa | 0.05 |
| Pressure coefficient | L/min/MPa | 8.7 |
| Water passing flow rate | ml/min | 435 |
| Water passing amount | L | 5 |
| Water passing time | h | 0.2 |
| Blank value | ng/L | <10 |
| Lower limit of quantification required | ng/L | 0.1 |
| Concentration factor | — | 100 |
| Water passing amount of eluent | ml | 50 |
| Water passing amount required | L | 5 |

In Example 10, it was possible to measure the content of B in the test water 3. On the other hand, the ultrapure water sampled by bottle was analyzed by ICP-MS for reference, but reliable results could not be obtained because the lower limit of quantification of ICP-MS was 10 ppt.

REFERENCE SIGNS LIST

10 Raw water
11 Ultrapure water production apparatus
12 Use point
13 Pipe for transferring ultrapure water
14 Pipe for withdrawing water to be analyzed
15 First branched pipe
16, 19, 27 Flow cell
17, 20, 28 Integrating flowmeter
18 Second branched pipe
21 Ultrapure water
22 Eluent
23 Introduction pipe for eluent
24, 25 Collected eluent
26 Analytical kit

The invention claimed is:

1. A method for analyzing a metal impurity content, comprising:
passing water to be analyzed through a monolithic organic porous anion exchanger, thereby allowing the monolithic organic porous anion exchanger to capture metal impurities in the water;
passing an eluent through the monolithic organic porous anion exchanger which has been allowed to capture metal impurities in the water to form a collected eluent containing the captured metal impurities eluted from the monolithic organic porous anion exchanger; and
measuring a content of each captured metal impurity in the collected eluent; wherein
the eluent is:
0.1 to 2.0 N nitric acid with a metal impurity content of 100 ppt or less, or
0.1 to 2.0 N hydrochloric acid with a metal impurity content of 100 ppt or less.

2. A method for analyzing a metal impurity content, comprising:
passing water to be analyzed through a monolithic organic porous cation exchanger, thereby allowing the monolithic organic porous cation exchanger to capture metal impurities in the water;
passing an eluent through the monolithic organic porous cation exchanger which has been allowed to capture metal impurities in the water to form a collected eluent containing the captured metal impurities eluted from the monolithic organic porous cation exchanger; and
measuring a content of each captured metal impurity in the collected eluent; wherein
the eluent is:
0.1 to 2.0 N nitric acid with a metal impurity content of 100 ppt or less, or
0.1 to 2.0 N hydrochloric acid with a metal impurity content of 100 ppt or less.

3. A method for analyzing a metal impurity content, comprising:
passing water to be analyzed firstly through a monolithic organic porous cation exchanger and then through a monolithic organic porous anion exchanger, or firstly through a monolithic organic porous anion exchanger and then through a monolithic organic porous cation exchanger, thereby allowing the monolithic organic porous cation exchanger and the monolithic organic porous anion exchanger to capture metal impurities in the water;
passing an eluent
firstly through the monolithic organic porous cation exchanger and then through the monolithic organic porous anion exchanger which have been allowed to capture metal impurities in the water, or
firstly through the monolithic organic porous anion exchanger and then through the monolithic organic porous cation exchanger which have been allowed to capture metal impurities in the water,
to form a collected eluent containing the captured metal impurities eluted from the monolithic organic porous cation exchanger and the monolithic organic porous anion exchanger; and
measuring a content of each captured metal impurity in the collected eluent; wherein
the eluent is:
0.1 to 2.0 N nitric acid with a metal impurity content of 100 ppt or less, or
0.1 to 2.0 N hydrochloric acid with a metal impurity content of 100 ppt or less.

4. The method for analyzing a metal impurity content according to claim 2, wherein the water to be analyzed contains at least ionic impurity elements and metal impurity fine particles as metal impurities.

5. The method for analyzing a metal impurity content according to claim 2, wherein an initial content of the metal impurities in the water to be analyzed is 1.000 ppt or less.

* * * * *